(12) United States Patent
Dutton et al.

(10) Patent No.: US 8,673,224 B2
(45) Date of Patent: Mar. 18, 2014

(54) APPARATUS FOR SYNTHESIS AND ASSAYING OF MATERIALS

(75) Inventors: Justin James Dutton, Yuba City, CA (US); Kenneth J. Micklash, II, Solana Beach, CA (US); Steven Kaye, San Diego, CA (US); Mark Bailey, San Diego, CA (US)

(73) Assignee: Wildcat Discovery Technologies, Inc., San Diego, CA (US)

( * ) Notice: Subject to any disclaimer, the term of this patent is extended or adjusted under 35 U.S.C. 154(b) by 473 days.

(21) Appl. No.: 12/902,344

(22) Filed: Oct. 12, 2010

(65) Prior Publication Data

US 2012/0087833 A1 Apr. 12, 2012

(51) Int. Cl.
 *B01J 19/02* (2006.01)

(52) U.S. Cl.
 USPC .................................... 422/130; 422/82.12

(58) Field of Classification Search
 USPC ............................. 422/130, 82.12, 552, 553
 See application file for complete search history.

(56) References Cited

U.S. PATENT DOCUMENTS

| | | | |
|---|---|---|---|
| 3,591,362 A | 7/1971 | Benjamin | |
| 5,482,524 A | 1/1996 | Nakano et al. | |
| 5,792,423 A | 8/1998 | Markelov | |
| 5,859,356 A | 1/1999 | Scheppers et al. | |
| 6,119,534 A | 9/2000 | Dinsmore | |
| 6,126,097 A | 10/2000 | Chen et al. | |
| 6,258,930 B1 | 7/2001 | Gauch et al. | |
| 6,350,414 B1 | 2/2002 | Ballin et al. | |
| 6,514,478 B2 | 2/2003 | Zaluska et al. | |
| 6,635,441 B2 | 10/2003 | Downs et al. | |
| 6,667,009 B1 | 12/2003 | Desrosiers | |
| 6,817,558 B1 | 11/2004 | Karlsson | |
| 6,826,549 B1 | 11/2004 | Marks et al. | |
| 6,852,289 B2 | 2/2005 | Gordon et al. | |
| 6,878,344 B2 | 4/2005 | Mansky et al. | |
| 2002/0048536 A1* | 4/2002 | Bergh et al. | 422/130 |
| 2003/0205636 A1 | 11/2003 | Karlsson et al. | |
| 2005/0090019 A1 | 4/2005 | Wendelbo | |
| 2005/0287573 A1 | 12/2005 | Stafslien | |
| 2007/0031295 A1 | 2/2007 | Downs | |
| 2007/0178019 A1 | 8/2007 | Downs | |
| 2008/0085221 A1 | 4/2008 | Downs | |

FOREIGN PATENT DOCUMENTS

| | | |
|---|---|---|
| DE | 10125126 A1 | 11/2002 |
| EP | 1323472 A2 | 7/2003 |
| WO | 03047744 A1 | 6/2003 |
| WO | 2007019226 A2 | 2/2007 |

OTHER PUBLICATIONS

PCT Search Report dated Dec. 20, 2011 for PCT/US2011/054845 filed Oct. 5, 2011.

(Continued)

*Primary Examiner* — Natalia Levkovich
(74) *Attorney, Agent, or Firm* — Quinn Law Group, PLLC

(57) ABSTRACT

An apparatus for synthesis and assaying of materials is provided that significantly improves throughput efficiency by allowing for material synthesis and assaying in the same assembly while possessing the ability to reach higher pressures and higher temperatures than existing designs capable of synthesis and assaying in the same assembly. In addition, the apparatus provides for gas flow over the material sample, allowing for a number of materials to be synthesized within the apparatus by gas synthesis.

16 Claims, 14 Drawing Sheets

(56) References Cited

OTHER PUBLICATIONS

Glen Mills Inc., Product Showcase: Planetary Ball Mill, www.glenmills.com/product_showcase/dry-fine planetary.shtml.

Craig M. Jensen, Satoshi Takara, "Catalytically Enchanced Systems for Hydrogen Storage", 2000 Proceedings of the 2000 Hydrogen Program Review, NREL/CP-57028890.

C.M. Jensen, et al., "Catalytically Enchanced Systems for Hydrogen Storage", Proceedings of the 2002 US DOE Hydrogen Program Review, NREL/CP-610-32405.

Gennari et al., "Hydrogen Storage Using Mg Based Alloys Produced by Mechanical Alloying", Conference: "Renewable Resources and Renewable Energy: A Global Challenge", Jun. 10, 2004.

Bossel et al., "The Future of the Hydrogen Economy: Bright or Bleak?, 2003 Fuel Cell Seminar", Apr. 15, 2003.

Urretavizcaya et al., "Mg—Ni Alloys for Hydrogen Storage Obtained by Ball Milling", Latin American Applied Research, 32: 289-294 (2002).

Dymatron, Inc., "Megapact and Megamill-5 Multi-Role Laboratory Processing Equipment", http://www.dymatron.com/megamill.html.

Peterson Macine Inc., "Attomill Sonic Ball Mill Grinder", OCETA Environmental Technology Profiles, http://oceta.on.ca/profiles/peterson/peterson_tech.thml.

Retsch, "Size Reduction and Homogenization with Ball Mills", Aug. 2004.

U.S. Appl. No. 11/841,768, Downs, "High Throughput Mechanical Alloying and Screening", filed Aug. 20, 2007.

U.S. Appl. No. 12/902,350, "Apparatus for Synthesis and Assaying of Materials with Temperature Control Assembly", filed Oct. 12, 2010.

\* cited by examiner

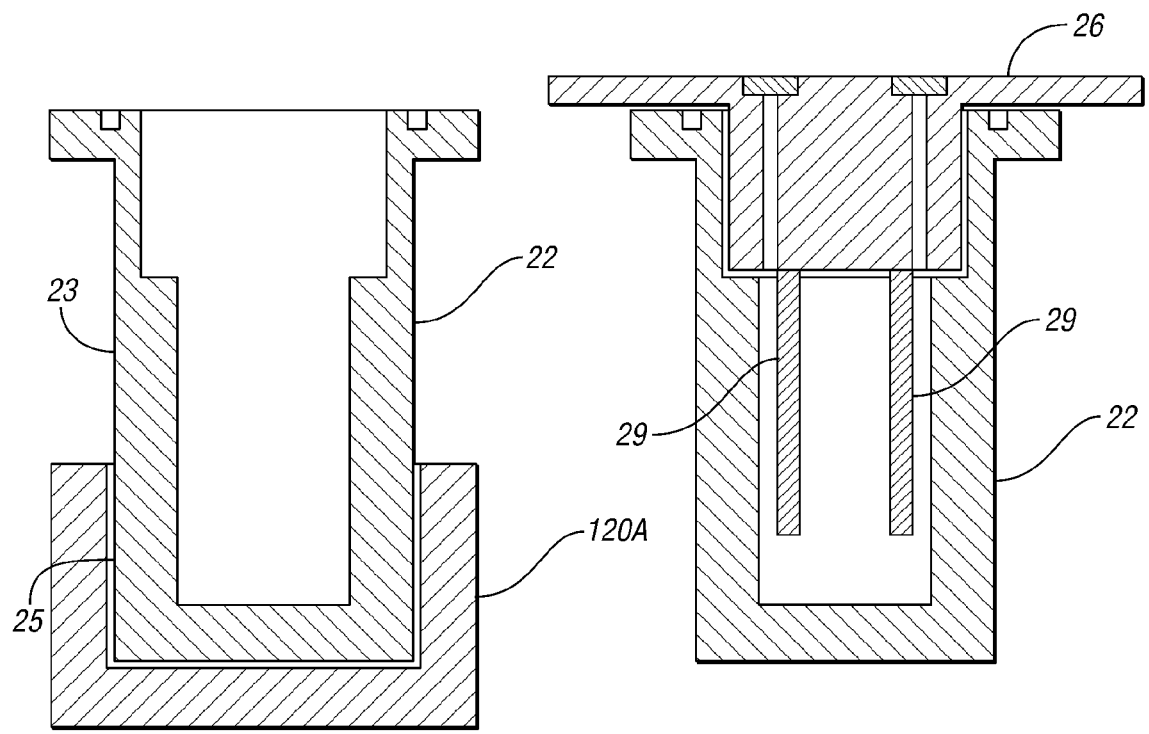
FIG. 11
FIG. 12
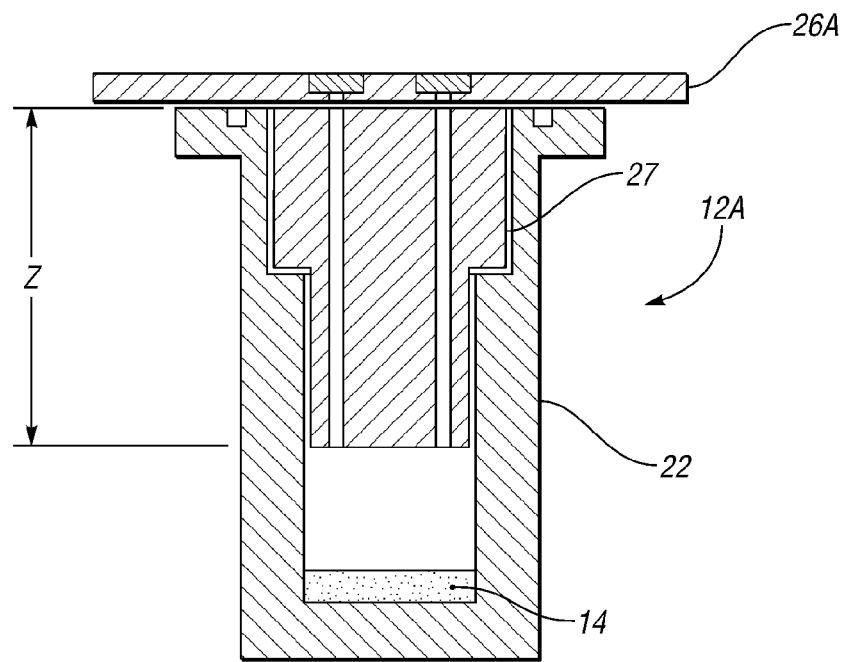
FIG. 14

APPARATUS FOR SYNTHESIS AND ASSAYING OF MATERIALS

TECHNICAL FIELD

The invention relates to an apparatus for synthesis and gas assaying of materials.

BACKGROUND

The success of high throughput synthesis and analysis of materials to identify composition and/or processing-property relationships is partially dependent on the reliability of the synthesis and assaying equipment, and the efficiency of the methods performed. Inherent limitations of the equipment used can directly limit the ability to explore a wide variety of materials. For example, most devices used for materials discovery do not implement an assembly in which the material can be both synthesized and assayed without disassembly. Rather, existing devices capable of high pressures and high temperatures typically require material transfer after synthesis (via ball milling, etc) into testing devices. Known devices that are designed to eliminate material transfer after synthesis cannot achieve sufficiently high pressures and temperatures desired for some particular material characterizations and/or synthesis processes.

SUMMARY

An apparatus for synthesis and gas assaying of materials is provided that significantly improves throughput efficiency by allowing for material synthesis and assaying in the same assembly while possessing the ability to reach higher pressures and higher temperatures than existing designs capable of synthesis and assaying in the same assembly. In addition, the apparatus provides for gas flow over the material sample, allowing for a number of materials that require gas flow during synthesis to be synthesized within the apparatus.

Specifically, the apparatus includes a well assembly having a well that is configured to contain material. The well assembly is configured such that the material can be synthesized within the well. The apparatus further includes a measurement device operatively connected to the well assembly that is configured to provide gas flow to the well for use in measuring at least one property of the material in the well. The apparatus is operable at temperatures within the well greater than about 550 degrees Celsius (° C.) and pressure within the well greater than about 150 Bar. The measurement device may connect to a multitude of well assemblies, allowing for parallel testing of multiple materials.

The apparatus is capable of material synthesis and assaying in the same assembly, eliminating the need for material transfer after synthesis. The apparatus includes a well assembly which can be used for synthesis in a separate device such as a shaker mill or a ball mill. The apparatus may also be used to assay materials synthesized outside of the well assembly through various means. The apparatus can reach material temperatures greater than about 550° C. and pressures greater than about 150 Bar while maintaining use of elastomeric seals between components. This allows for reliable, relatively inexpensive seals despite material temperatures significantly above rated elastomeric seal temperatures. Alternate embodiments may implement the use of alternative sealing methods such as gasket sheets, gasket makers or mechanical seals, although not limited to such.

The high temperature and high pressure capabilities of the apparatus are due in part to a temperature control assembly of the measurement device that may include a heater positioned to heat a bottom portion of the well. The bottom portion is characterized by a surface area in contact with the heater. Furthermore, a spring may be positioned to bias the heater against the bottom portion, thus accommodating for dimensional variation in the components to ensure efficient heat transfer from the heater to the well. The temperature control assembly may include an insulator configured to surround an outer surface of the side wall of the well to minimize heat transfer from the well through the side wall.

One of the elastomeric seals used to seal the components of the apparatus is supported at a circumferential flange of the well and is configured to seal a first component of the well assembly to a second component of the well assembly. An adapter abuts the flange and is characterized by a thermal conductivity greater than the thermal conductivity of the flange to promote heat transfer out of the flange. The adapter may have a stepped opening configured such that the side wall of the well extends through the opening when the flange abuts the adapter at the stepped opening. At least some abutting surfaces of the adapter and the flange may be uncoated to further promote heat transfer from the flange to the adapter.

The well may have a step at an inner diameter such that a thickness of the side wall at the flange is less than a thickness of the side wall adjacent to the bottom surface, thereby increasing the thermal mass near material in the well, and minimizing the thermal mass near the flange. This acts to minimize the temperature gradient in the region of the material to be characterized while maximizing the temperature gradient from the step to the flange, minimizing the flange (and thus the seal) temperature.

The well assembly may include a wear plate configured to fit with the well at the stepped diameter and to protrude into the well at the step, thereby maintaining the material in the bottom portion of the well below the step. The wear plate may also incorporate features to enhance gas circulation during gas flow though the well, as later discussed. In some embodiments it may be desirable to omit the protrusion of the wear plate into the well, as later discussed.

The apparatus is also capable of flowing gas across a material sample in the well, a process necessary for a variety of material synthesis processes, including materials being treated to a number of heat treatment processes. The capability of gas flow across the material sample expands the options for material synthesis in the same assembly used for assaying. The apparatus is also capable of periodic turnover of the system gas at any desired frequency.

Accordingly, the apparatus enables significant improvements in high throughput materials discovery because it implements an assembly (referred to as a well assembly) in which both material synthesis (either on separate devices or within the well assembly) and assaying can be performed while allowing for material temperatures in excess of 550° C. and pressures exceeding 150 Bar. The capabilities of gas flow across a sample material, elimination of material transfer between synthesis and assay and the achievable pressures and temperatures make this device unique from existing devices in the field.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 11 is a schematic cross-sectional illustration of an alternate embodiment that may be used to heat the well;

FIG. 12 is a schematic cross-sectional illustration of an additional feature extruding from the wear plate that may be implemented to improve gas circulation within the well;

FIG. 14 is a schematic cross-sectional illustration of an alternate embodiment within the well assembly where a flat wear plate is used in conjunction with an insulating component placed inside the well.

DETAILED DESCRIPTION

Figure 1A:
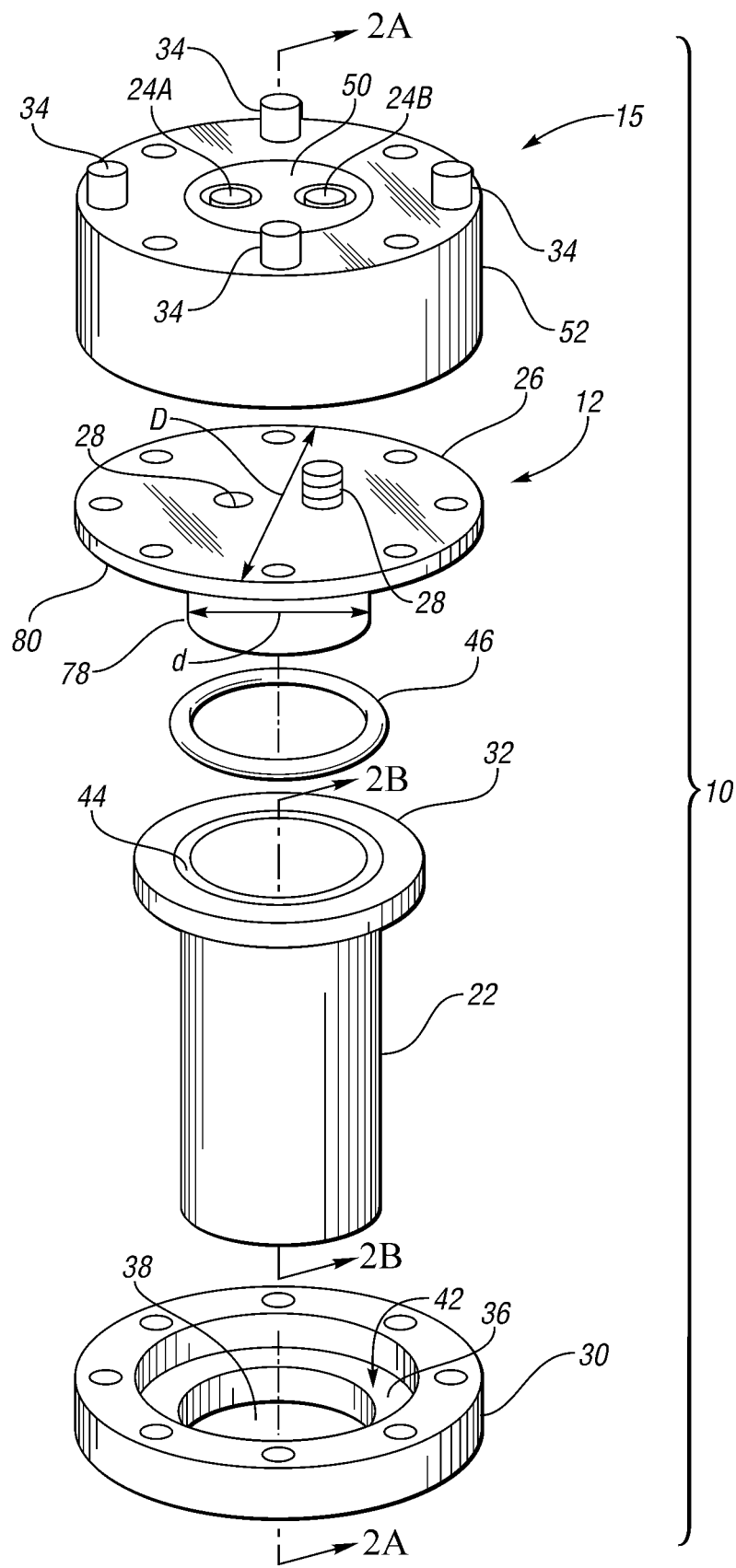
FIG. 1A is a schematic illustration in exploded perspective view of a portion of the material synthesizing and assaying apparatus, including a well assembly that includes a lid assembly, a subassembly within the well assembly, and a wear plate.

A gas synthesis and assaying apparatus 10, sometimes referred to herein as an assay device, includes many components which, in combination, provide measurement of various material properties under various temperatures and pressures. The apparatus 10 may be configured to test a multitude of materials in parallel, thereby increasing the high throughput capabilities of the apparatus 10. Referring to FIG. 1A, the apparatus 10 includes a mobile well assembly 12 in which the material 14 to be assayed is contained (see FIG. 2A, 5A). A lid assembly 15 is a subassembly of the well assembly 12. The apparatus 10 further includes a measurement device 16 having a temperature control assembly 17 (see FIGS. 6A and 6B), a gas delivery and control system 18 (see FIG. 8B), and a temperature controlled enclosure assembly 20 that partially encloses the gas delivery and control system (see FIG. 8A). The gas delivery and control system 18 is a multichannel system of calibrated volumes and data acquisition devices, with which the well assembly 12 is in gaseous communication with during an assay. An "assay" is any data collection process performed by the measurement device which ultimately leads to characterization of various material properties.

As further described below, the well assembly 12 includes several components which assemble with a number of elastomeric seals to create gas tight seals between components. Within the well assembly 12 is a well 22 (seen in FIG. 1A) in which the material 14 to be assayed is contained (see FIGS. 2A and 2B). For certain types of synthesis, before the well assembly 12 is brought to the measurement device 16 for an assay, several steps must be performed. These steps vary according to the material being characterized or assay process being performed. For instance, a typical metal hydride procedure begins with a disassembled well assembly 12 in an atmosphere-controlled chamber, often referred to as a glove box. The glove box is filled with an inert gas such as argon to allow handling and transfer of air-sensitive materials. Although not all metal hydride materials are air sensitive, material transfers are typically done in an inert atmosphere. Within the glove box, elements and/or compounds in powder or liquid form are dispensed into the well 22 in various relative quantities such that a material composite or mixture will be produced after synthesis. If necessary, one or more ball bearings can be placed inside well 22 either before or after the elements and/or compounds are added. In some cases, objects of alternative shapes may be placed inside well 22; these may include shapes such as rods, cylinders, ovals, and so forth.

While still in the glove box, the well assembly 12 is reassembled so that any air sensitive materials are isolated, and the assembly 12 can safely be removed from the glove box. In a typical metal hydride process, before assembling the well assembly, one or more ball bearings, which are often required for a mechanical alloying synthesis process, can be added to the well. After the appropriate contents are added (in any order), the well assembly 12 can remain sealed and assembled through any subsequent synthesis and/or assay processes. The well assembly 12 may now be fastened into a shaker mill or ball mill (not shown) which will react, mix and/or homogenize the components to create a product such as a mixture, composite or a compound. After the synthesis process is complete (through ball milling or other methods), the well assembly 12 is brought to the measurement device 16 to be assayed.

By contrast, certain types of material testing applications are able to use the apparatus 10, without requiring a separate ball mill or other device, to synthesize the material. For example, as described further below, materials that are synthesized by heating under a gas flow may be synthesized within the well assembly 12 with the well assembly 12 assembled to the measurement device 16 rather than placed in a ball mill. Samples may also be synthesized through alternative methods and then placed in well assembly 12 for measurement on measurement device 16.

Well Assembly

After the appropriate contents are added (in any order), the well assembly 12 can remain sealed and assembled through any subsequent synthesis and/or assay processes. The well assembly 12 has been designed such that material synthesis (whether occurring in a mechanical alloying process, such as ball milling, or in the assay device, such as by heating material under a gas flow, as later described) can be accomplished with the well assembly 12 fully assembled. Thus, the well assembly 12 is designed to allow both material synthesis and assay procedures to be done with the material 14 in the well assembly 12. When assembled, the well 22 in which material 14 is contained is air tight, allowing for storage and transfer of air sensitive materials in standard atmosphere conditions. This allows procedures such as ball milling and assaying to occur outside of an inert atmosphere such as a glove box.

Figure 1B:
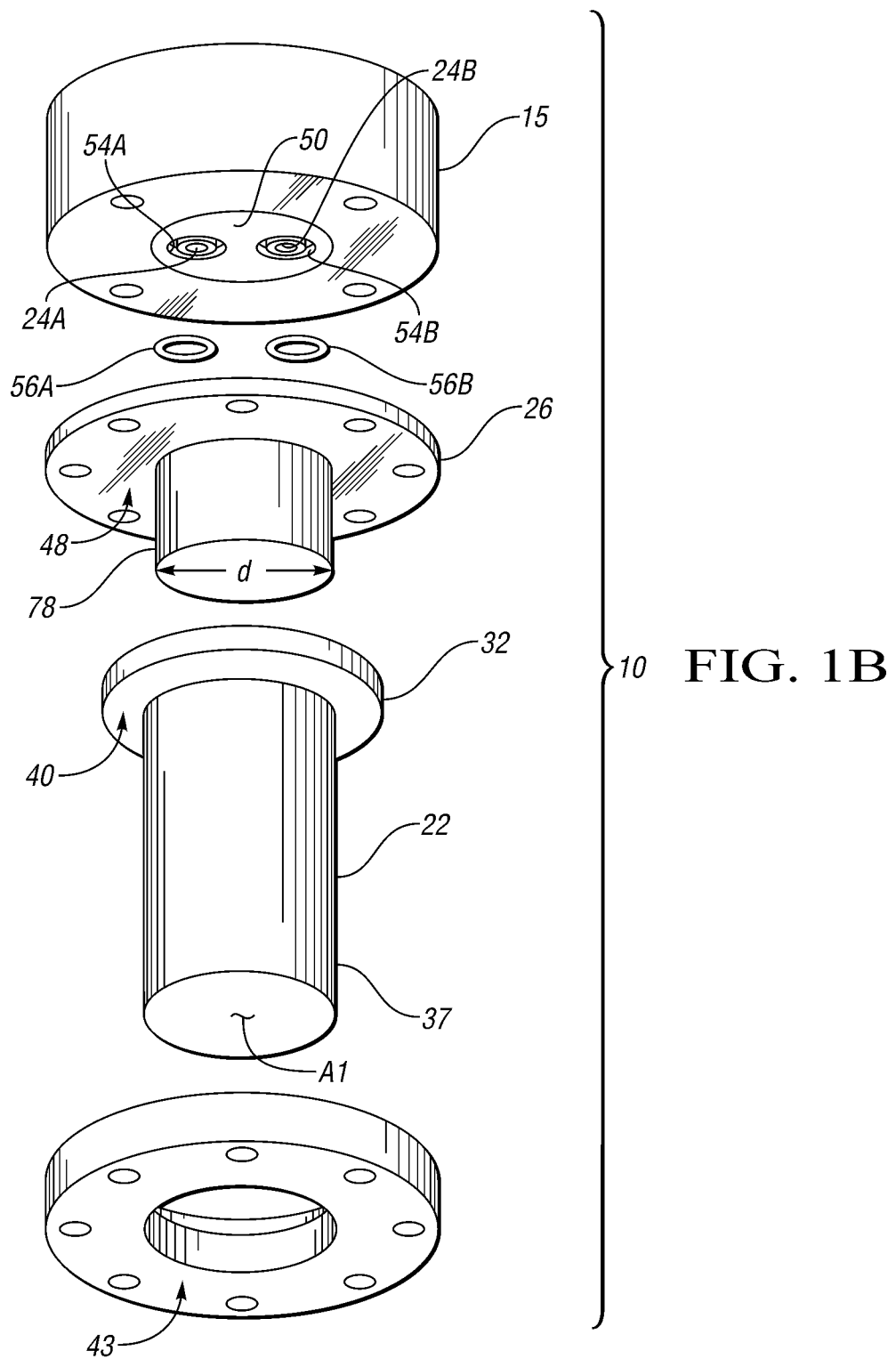
FIG. 1B is a schematic illustration in exploded view from an alternate perspective of the portion of the material synthesizing and assaying apparatus of FIG. 1A.

FIGS. 1A and 1B illustrate exploded views of the well assembly 12 including the lid assembly 15, a subassembly of the well assembly 12, although not shown in exploded view. The well assembly 12 includes the lid assembly 15 in which an inlet valve 24A and an outlet valve 24B hold pressure within the well assembly 12, as further described below. Alternately, as also described below, only one valve, such as inlet valve 24A, may be used, with the single valve functioning as both an inlet and outlet. Valves 24A and 24B may include valves such as Schrader® valves, presta valves or custom valves, although not limited to such. The Schrader® valve is available from Schrader-Bridgeport, Inc. in Altavista, Va. A Schrader® valve generally has a valve stem into which a valve core is threaded. The valve core is a poppet valve assisted by a spring.

A wear plate 26 is shown below the lid assembly 15. Wear plate 26 supports filters 28 residing therein such that solid elements do not escape the well 22 during an assay, thereby preventing clogged lines or valve failures in the measurement device 16. Below the wear plate 26 is the well 22 in which material 14 (see FIG. 2A), and, if synthesis is by ball milling, one or more ball bearings reside. The well assembly 12 includes a heat conducting annular adapter 30 that mounts below a circumferential flange 32 of the well 22. The adapter 30 forms a step 36 at an inner diameter. A lower portion 37 of the well 22 is sized to extend through an opening 38 of the adapter 30, with a bottom surface 40 (see FIG. 1B) of the flange 32 abutting with and supported at an upper surface 42 (see FIG. 1A) of the step 36 when the well assembly 12 is assembled.

Fasteners 34 extend through aligned fastener openings of the lid assembly 15, the wear plate 26 and the adapter 30, to sandwich the wear plate 26 and the flange 32 between the lid assembly 15 and the adapter 30. The flange 32 has a circumferential groove 44 in which an elastomeric seal 46 is contained. When assembled, the elastomeric seal 46 seals the flange 32 to the bottom surface 48 of the wear plate 26 (see FIG. 1B). As further described below, the lid assembly 15 has an inner component 50 fit within an outer component 52. The inner component 50 carries the valves 24A, 24B. Grooves 54A, 54B are formed by the inner component 50 around the valves 24A, 24B. Additional elastomeric seals 56A, 56B are sized to reside in the grooves 54A, 54B, respectively (shown seated in the grooves 54A and 54B in FIGS. 2A and 3A) to seal the lid assembly 15 to the wear plate 26 when the well assembly 12 is assembled.

Figure 2A:
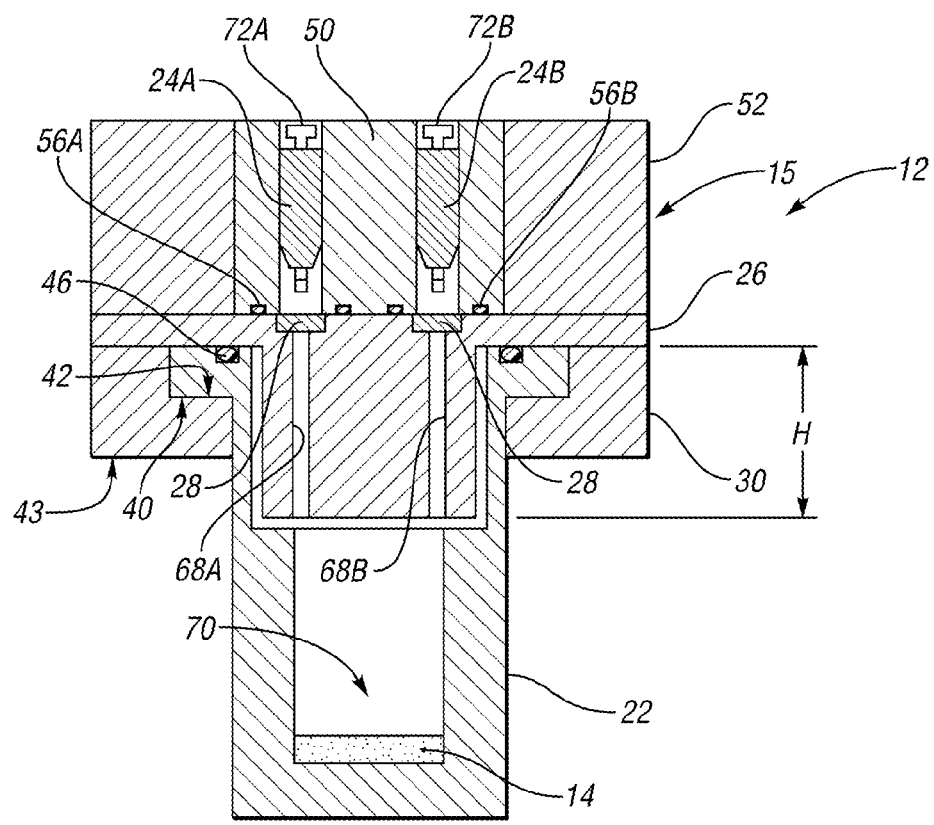
FIG. 2A is a schematic cross-sectional illustration of the assembled well assembly taken at the lines 2A of FIG. 1A.
Figure 2B:
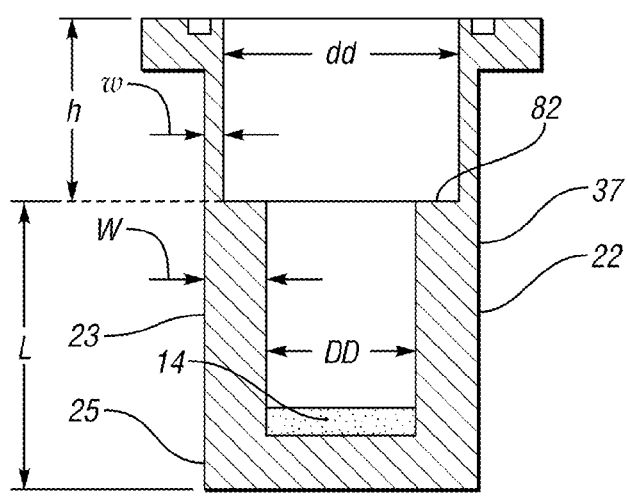
FIG. 2B is a schematic cross-sectional illustration of a well of the well assembly taken at the lines 2B of FIG. 1A.
Figure 3A:
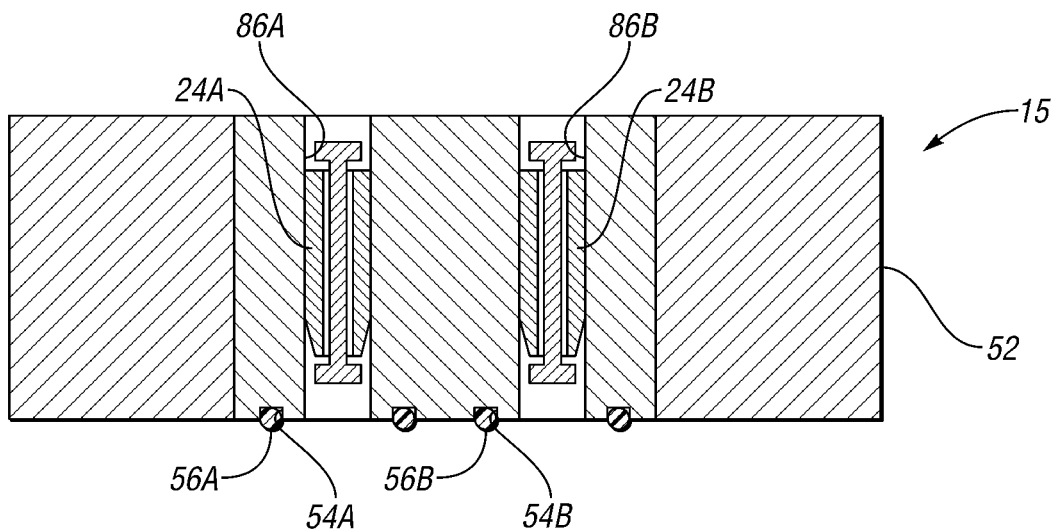
FIG. 3A is a schematic cross-sectional illustration of the lid assembly taken at lines 3A in FIG. 3B.

FIG. 2A shows a cross-section of the assembled well assembly 12 with adapter 30, taken at the lines 2A in FIG. 1A. Here, gas paths through the lid assembly 15 and the remainder of the well assembly 12, as well as sealing surfaces at the elastomeric seals 46, 56A, 56B, are clearly illustrated. Specifically, a gas inlet flow path is through the valve 24A (when opened, as shown in FIG. 3A and described below), through the filter 28 and a channel 68A in the wear plate 26 to an internal cavity 70 of the well 22. A gas outlet flow path is from the cavity 70 through a channel 68B in the wear plate 26 and through outlet valve 24B, when opened as shown in FIG. 3A. In alternate embodiments it may be desirable to incorporate flow-directing features 29 on the bottom of wear plate 26 (seen in FIG. 12) to improve air circulation through the well when under gas flow. Features 29 such as these may be necessary to ensure thorough flow over material 14 at the bottom of well 22. Feature 29 may extend further into well 22 from the bottom surface of wear plate 26, ensuring that gas flow from inlet to outlet is directed across the surface of material 14. Feature 29 may be a machined feature of wear plate 26 or it may be an additional component mated with wear plate 26 through the use of an epoxy, welding, press fit or other means.

The valves 24A, 24B are configured to hold pressure within the assembly 12 when closed, as shown in FIG. 2A. When the well assembly 12 is installed in the measurement device 16, valve stems 72A, 72B are depressed from above by actuator pins 96A, 96B of cap plate assembly 84 (shown and discussed with respect to FIG. 4A, 4B), opening valves 24A, 24B and providing gaseous communication between well assembly 12 and the corresponding measurement device 16, as further described below.

Wear plate 26 may have a stepped diameter, as shown in FIG. 1A, formed by a protruding portion 78 of relatively small diameter d, and a flange portion 80 of relatively large diameter D. The diameter d of the protruding portion 78 matches closely to an inner diameter dd of an upper portion of well 22 (see FIG. 2B). Depth H (see FIG. 2A) of protruding portion 78 matches closely to depth h (see FIG. 2B) of a step 82 in wall thickness of well 22. Specifically, the well 22 has a side wall 23 extending from the bottom portion 25 of the well 22. The side wall 23 has a thickness W below the step 82 and a lesser wall thickness w above the step 82. When assembled, this ensures material 14 being assayed is contained in the higher temperature lower portion 37 of well 22 (while also minimizing the temperature gradient of the sample material 14), as later described. It is highly desirable for material temperature to be uniform, as many analysis calculations must assume that all of the material 14 is at the same temperature. Accuracy of the corresponding measurement may be reduced as the material temperature becomes less homogeneous. Wear plate 26 is preferably a hard material capable of withstanding repeated impact during mechanical alloying without permanent deformation, although not limited to such. In some instances, the desirable wear plate material may be stainless steel, aluminum, or a number of other materials. The wear plate 26 must also withstand the elevated temperatures to which it is exposed within the well assembly. For example, wear plate 26 could be hardened steel, ceramic, etc. As discussed above, wear plate 26 provides dual independent pathways via channels 68A, 68B that allow independent gas flow paths in and/or out of cavity 70 of well 22. As further discussed below, a wear plate with a single valve and channel may also suffice in some embodiments.

FIG. 14 illustrates an alternate embodiment of a well assembly 12A in which a flat wear plate 26A may be used in conjunction with an insulating component 27 in place of wear plate 26 which protrudes into well 22. It may be desirable to implement insulating components 27 of various heights Z depending on the volume of material 14 at the bottom of well 22. The alternate embodiment depicted in FIG. 14 enhances the flexibility of the apparatus 10 in terms of material characterization capability.

Figure 3B:
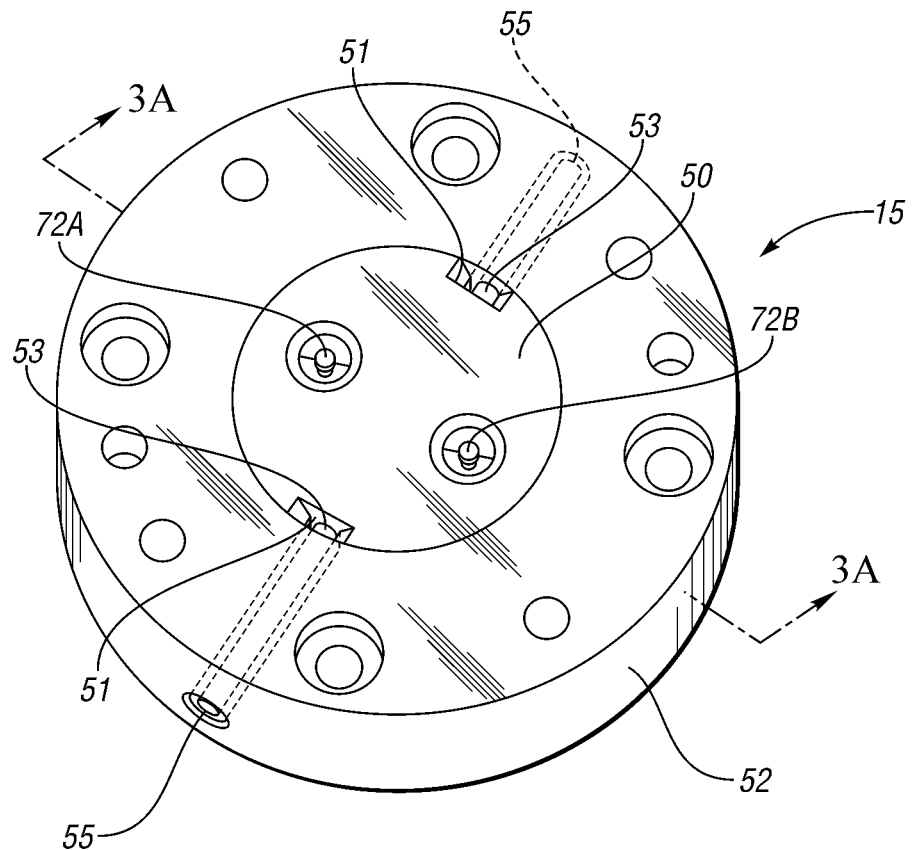
FIG. 3B is a schematic perspective view of the lid assembly.
Figure 4A:
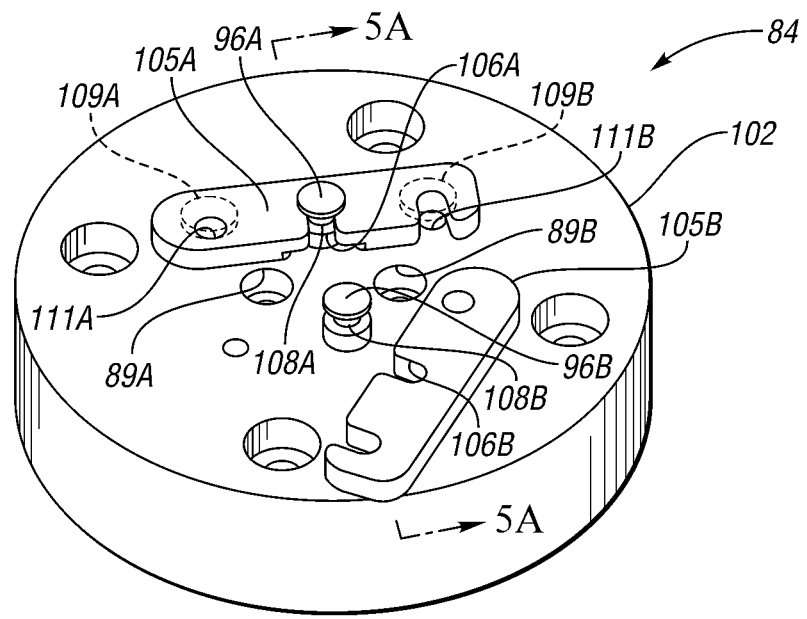
FIG. 4A is a schematic perspective top view of a cap plate assembly of the apparatus, including actuator pins and cams.
Figure 4B:
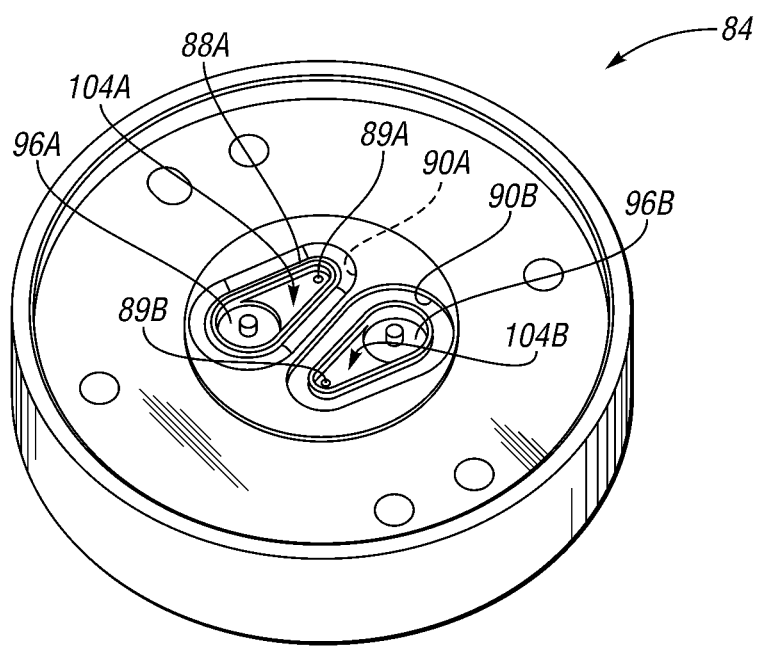
FIG. 4B is a schematic perspective bottom view of the cap plate assembly including elastomeric seal grooves.

Referring again to FIG. 2A, lid assembly 15 provides a lid for the assembled well 22, adapter 30 and wear plate 26, while acting as an interface with the assay measurement device 16, and specifically with a cap plate assembly 84 portion of the measurement device 16, discussed further with respect to FIGS. 4A and 4B. The dual independent valves 24A, 24B of the lid assembly 15 are depicted in an open position in FIGS. 3A and 3B, and allow multiple gas routes into the well 22, as previously discussed. The face sealing orientation of elastomeric seals 56A, 56B in grooves 54A, 54B on the bottom surface of inner component 50 are shown.

Dual valves 24A, 24B within the lid assembly 15 expand the measurement possibilities of the apparatus 10. It may be desirable, for instance, to flow gas across a sample of material 14, a procedure necessary for synthesis of a number of materials, including some used for heat treatment of a number of materials. This can be accomplished with the assay measurement device 16 by treating one valve in lid assembly 15 as an inlet (inlet valve 24A) and the other as an outlet (outlet valve 24B). It may be desirable to provide an adjustable flow control device to achieve desired gas flow rates for applications such as gas flow degassing. It may also be desirable to connect the outlet valve 24B to additional analytical equipment such as a mass spectrometer. The well assembly 12 could also act as the terminal path by opening only one valve 24A or 24B in lid assembly 15. Further detail is provided below with respect to the gas delivery and control system 18 shown schematically in FIGS. 12 and 13, as well as options for eliminating the need for dual valves in the lid assembly 15 by pulsing gas through a single valve and one channel in the wear plate as both the inlet and the outlet.

Lid assembly 15 is an assembly consisting of two components (inner component 50 and outer component 52) which are pressed together (i.e., press fit to one another), or otherwise assembled. For the embodiment shown, the relative orientation of the two mating components 50, 52 must be accurate to ensure proper operation. This can be accomplished in several ways. For instance, the outer diameter of the inner component 50 can include slots 51 parallel to a center axis i.e., parallel to the channels 86A, 86B holding the valves 24A, 24B, respectively. The slots 51 are configured to align during assembly with dowel pins 53 (shown partially in phantom in FIG. 3B) inserted in openings 55 of the outer component 52. The inner component 50, referred to as the insert, can be pressed in and out of the outer component 52 somewhat easily, allowing for replacement if necessary. In some instances, lid assembly 15 could be made from a single component if desired.

Measurement Device

The measurement device 16 includes several components and subassemblies such as the temperature control assembly 17 and cap plate assembly 84, in which gaseous communication is created between the well assembly 12 and the remainder of the measurement device 16, as well as a gas delivery and control system 18, a system of volumes, valves and data acquisition devices which include pressure transducers and thermocouples. The measurement device may include components for multiple channels, allowing for parallel synthesis and/or assaying of multiple materials in a high throughput manner.

Figure 5A:
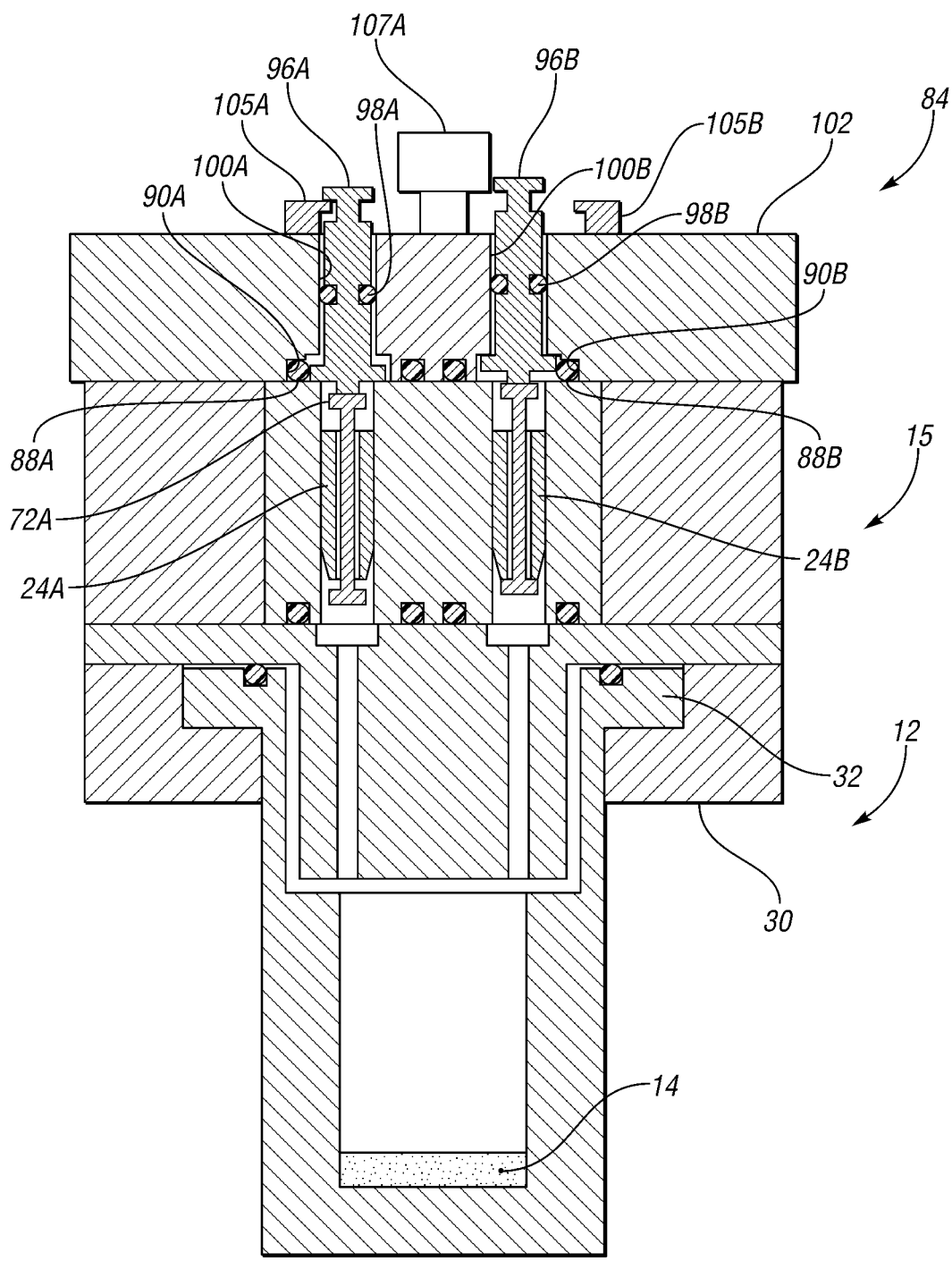
FIG. 5A is a schematic cross-sectional illustration of the well assembly of FIG. 2A with the cap plate assembly taken at the lines 5A of FIG. 4A.

The cap plate assembly 84 depicted in FIGS. 4A and 4B mates to the well assembly 12 with elastomeric seals 88A, 88B, as shown in FIG. 5A, in such a way that an air-tight seal is made between the gas flow paths of the cap plate assembly 84 and those of the well assembly 12. Referring to FIG. 4B, an underside of cap plate assembly 84 has grooves 90A, 90B in which face-sealing elastomeric seals 88A, 88B (one shown in FIG. 4B, both shown in FIG. 5A) are installed for an air-tight seal with lid assembly 15 of the well assembly 12. Elastomeric seal 88A surrounds the underside of the pin 96A and channel 100A, as well as gas flow inlet 89A and gas flow outlet 89B provided through a cap plate 102 of the cap plate assembly 84 (see, e.g., gas flow outlet 89B in FIG. 5B).

Referring to FIG. 4A, actuator pins 96A, 96B are generally cylindrically-shaped components in which shaft sealing elastomeric seals 98A, 98B (see FIG. 5A) create an air tight seal when installed in channels 100A, 100B formed in cap plate 102 of cap plate assembly 84. Valves 24A, 24B in the well assembly 12 are externally controlled (by the cap plate assembly 84) when the well assembly 12 is installed on the fixture 103 of the temperature control assembly 17 (see FIGS. 6A and 6B). Thus, gaseous communication between well assembly 12 and the measurement device 16 can be controlled through motion of actuator pins 96A, 96B, as illustrated in FIG. 5A. Specifically, referring to FIG. 4A, cam devices 105A, 105B include slots 106A, 106B that may be positioned to surround a narrowed portion 108A, 108B of the respective pins 96A, 96B. Two bolts 109A, 109B (shown in phantom in FIG. 4A) extend through openings 111A, 111B in the cam devices 105A and aligned openings in the cap plate 102. When the bolts are tightened, the cam device 105A depresses the pin 96A, opening valve 24A. Similar bolts (not shown) can extend through aligned openings in cam device 105B and cap plate 102, and can be tightened to depress pin 96B. In some embodiments, it may be desirable to automate the process of depressing pins 96A and 96B through a device such as a linear actuator driven by a stepper motor, electric motor, servo motor and the like. This may allow for automated control of the opening and closing of valves 24A and 24B.

Figure 5B:
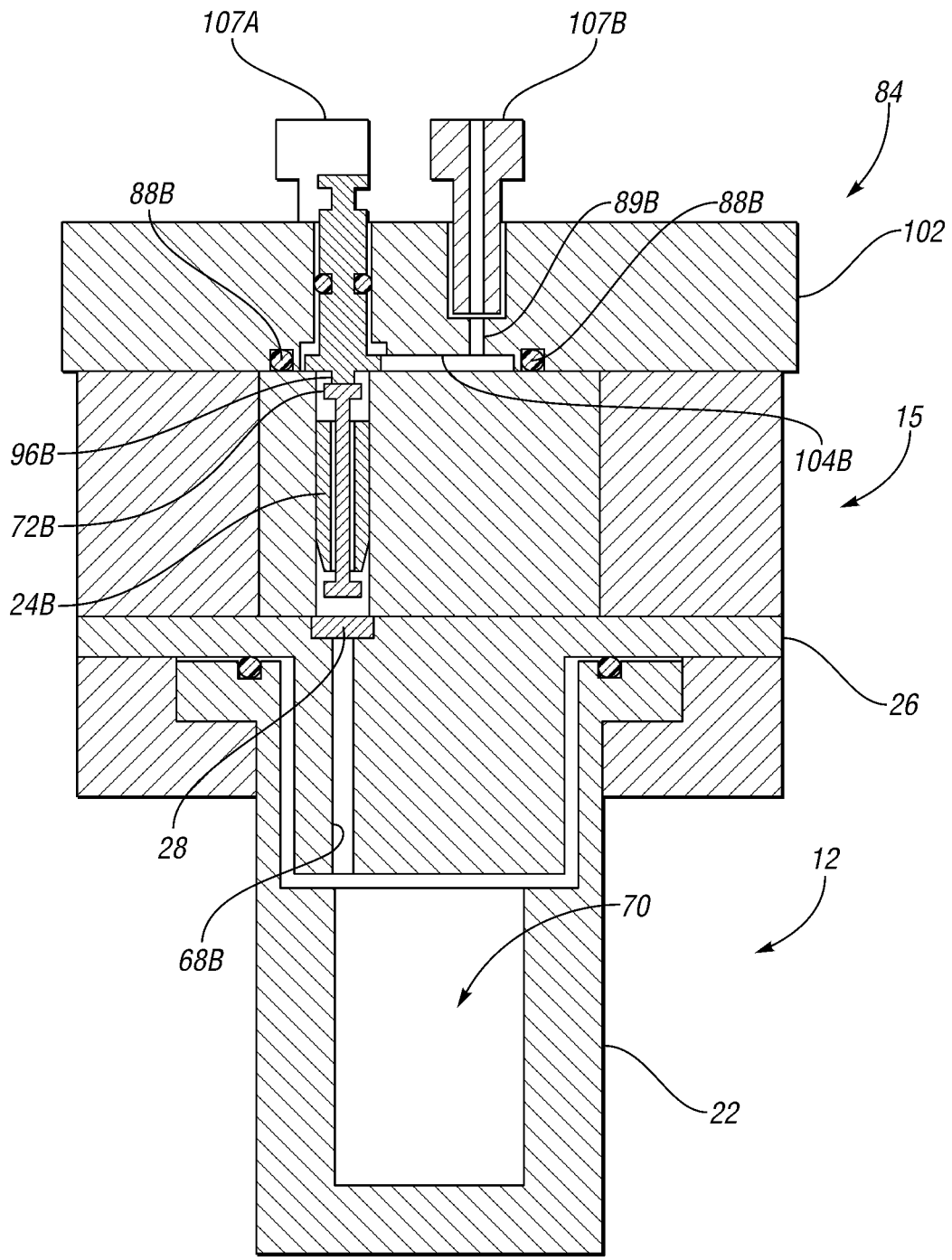
FIG. 5B is a schematic cross-sectional illustration of the well assembly and cap plate assembly showing a gas flow path between the cap plate assembly and the well assembly.

In FIG. 5A, valve 24A is shown open, with valve stem 72A depressed by pin 96A, and valve 24B is closed. FIG. 5B further illustrates a gas flow path, here a gas exit flow path, from cavity 70 through channel 68B of wear plate 26, through valve 24B (if stem 72B is depressed), laterally through a cavity 104B formed in the cap plate 102 (see also FIG. 4B), through gas flow outlet 89B, to a gas line 107B. Cavity 104B is surrounded by seal 88B, as is the outlet 89B. A gas inlet flow path from a gas line 107A is similarly created from the gas inlet 89A, laterally through a cavity 104A (see FIG. 4B), past valve 24A when depressed by pin 96A, and through channel 68B (see FIG. 2A) in wear plate 26. Essentially, the cap plate assembly 84 acts to complete the connection between the well assembly 12 and gas delivery and control system 18 of the measurement device 16.

Temperature Control Assembly

Figure 6A:
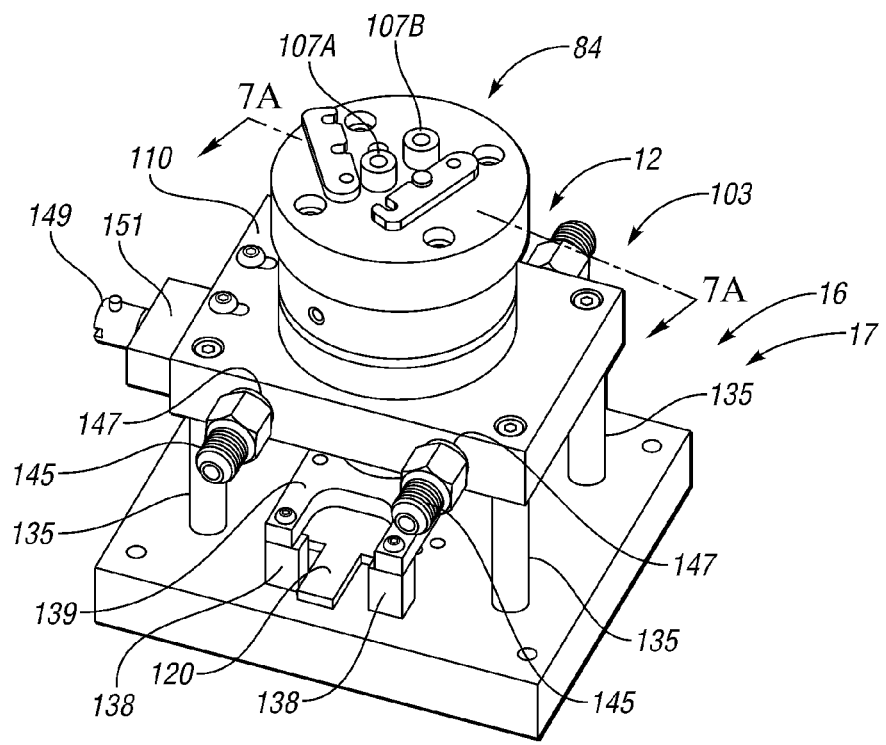
FIG. 6A is a schematic perspective illustration of the well assembly installed in a temperature control assembly of a measurement device of the apparatus.
Figure 6B:
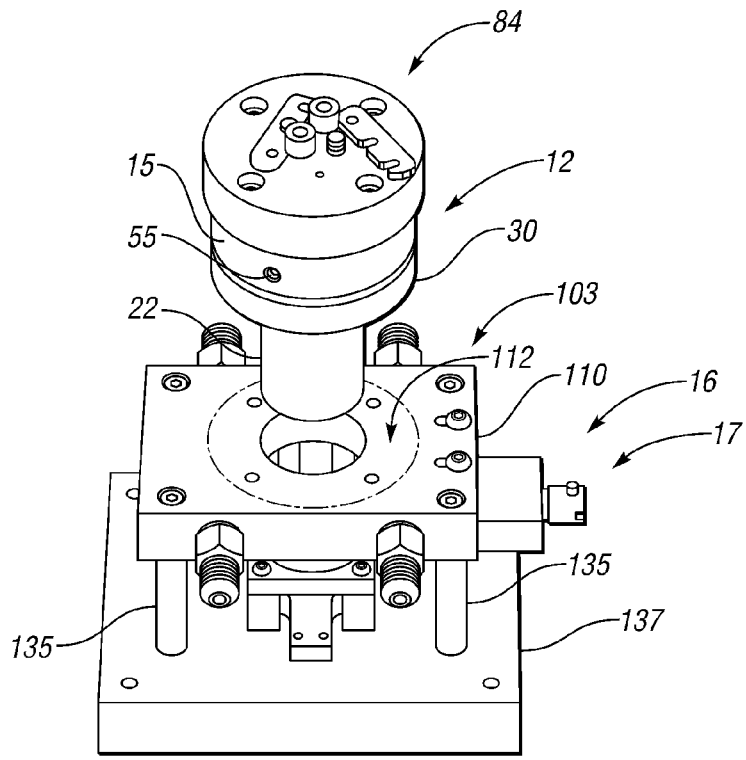
FIG. 6B is a schematic perspective exploded view of FIG. 6A.

FIG. 6A illustrates the well assembly 12, including lid assembly 15, connected to cap plate assembly 84, when installed in the temperature control assembly 17 of the measurement device 16. FIG. 6B further clarifies the portable nature of the well assembly 12 with cap plate assembly 84 and adapter 30 connected thereto and selective mounting to the fixture 103. With multiple fasteners, the fixture 103 acts to restrain the well assembly 12 while compressing elastomeric seals 88A, 88B (see FIG. 5A) between cap plate assembly 84 and lid assembly 15, ensuring an air-tight seal.

The fixture 103 includes a temperature controlled block 110. The adapter 30 contacts the surface of the temperature controlled block 110 at surface area 112, indicated in phantom, such that heat transfer out of the well assembly 12 can be controlled. The adapter 30 is preferably a material with a higher thermal conductivity than the flange 32 (shown abutting in FIG. 5A) to promote heat transfer out of the flange 32. The temperature of block 110 can be controlled through several means. For example, fluid lines in connection with a fluid temperature control device could be used. A chiller or heater/chiller unit could be used to accurately maintain fluid temperature through the temperature controlled block 110. To achieve desired heat transfer rates, the temperature control device could be pulsed on or off to allow higher, yet controlled temperatures of the temperature controlled block 110. This may be necessary, as many standard heating/refrigerating units only maintain fluid temperatures as high as approximately 70° C. A fan (not shown) mounted near the top half of the well assembly 12 could also be used to remove heat. Fan flow rate and orientation will depict final heat transfer rate. As with a chiller, this fan could also be pulsed on and off to achieve desired heat transfer properties.

Figure 7A:
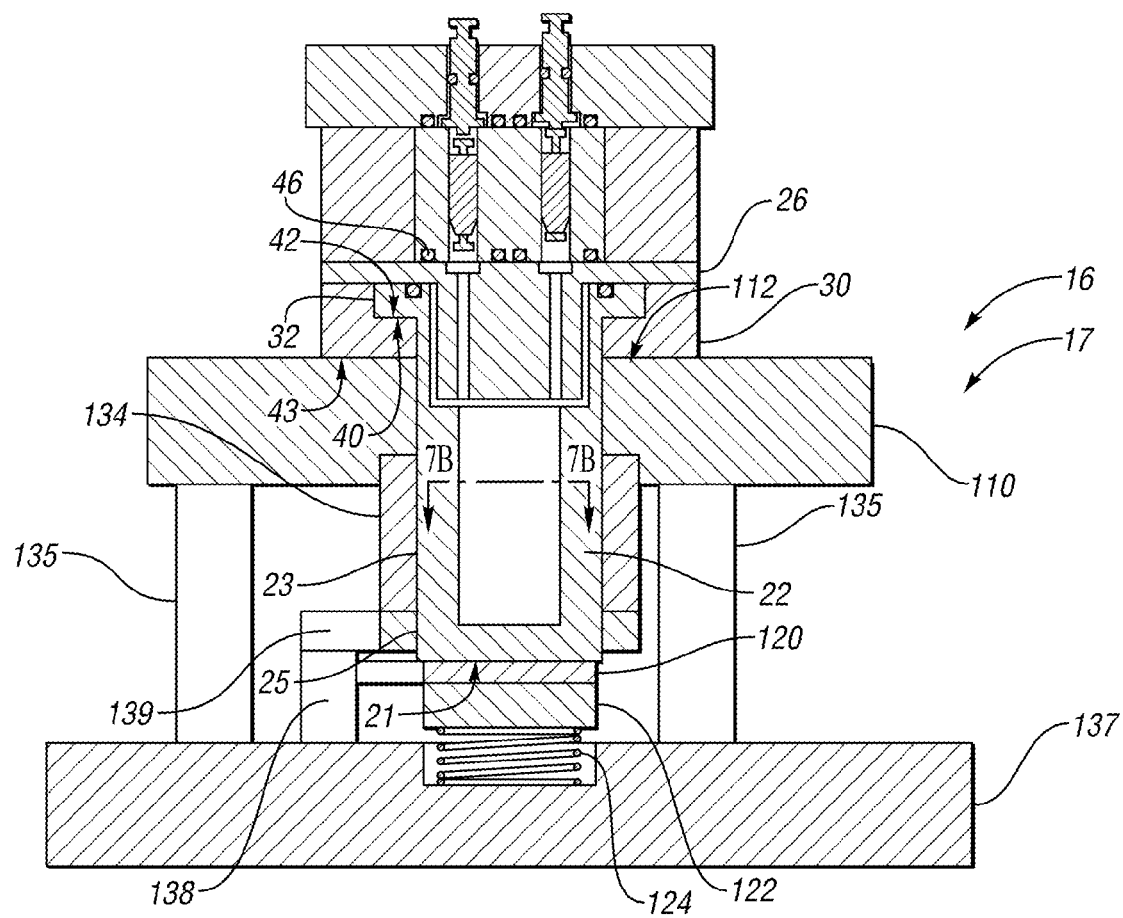
FIG. 7A is a schematic cross-sectional illustration of the well assembly installed in the temperature control assembly, taken at lines 7A of FIG. 6A, showing the heater, well and spring interfaces.
Figure 7B:
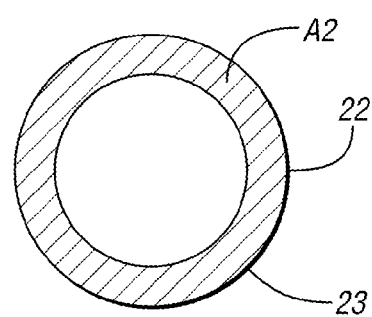
FIG. 7B is a schematic cross-sectional illustration of the well of FIG. 7A taken at the lines 7B.

FIG. 7A illustrates a heater 120 in contact with a surface area A1 of the bottom surface 21 of the bottom portion 25 of the well 22 (area A1 shown also in FIG. 1B) after installation of the well assembly 12 in the temperature control assembly 17. In order to maximize heat transfer between the heater 120 and well 22, the area A2, as shown in FIG. 7B, should be maximized without compromising the internal volume of well 22. For example, the area A2 could be the maximum size that still ensures that a predetermined minimum volume remains in the well 22. The predetermined minimum volume may depend on the material that will be synthesized in the well 22. As later described, selecting the size of area A2 in this manner promotes heat transfer and reduces the temperature gradient in the lower, thicker wall portion of well 22. Below the heater 120 is a ceramic insulator 122 and high temperature spring 124. The temperature control assembly 17 accounts for dimensional variances of different well assemblies 12 that may be inserted in the temperature control assembly 17, without affecting performance. Essentially, the spring 124 allows for length variances of the well assembly 12 by compressing as necessary to maintain a desirable spring force between the well assembly 12 and the heater 120, and thereby promote heat transfer as desired. Desirable spring force rates should allow for simple user installation of well assembly 12 into temperature control assembly 17 while providing good thermal contact between heater 120 and the bottom of well 22.

Referring to FIG. 11, an alternate embodiment of a heater 120A is configured to surround a portion of the side wall 23 of well 22, as well as contact the bottom portion. This may be desirable to further minimize the temperature gradient in the region where material 14 is contained.

Thus, the temperature control assembly 17 with well assembly 12 therein, as shown in FIG. 6A, allows for precise control of the well temperature, ultimately controlling the temperature of the sample material 14. The temperature of the material 14 in the well 22 is controlled to determine material properties such as uptake or release of hydrogen in a metal hydride for various temperature and pressure conditions. In some embodiments, a multitude of temperature control assemblies and well assemblies may be incorporated within a single assay device, allowing for parallel material characterization of a number of materials. This allows the assay device to characterize materials in a high throughput fashion. It may also be desirable to increase throughput by incorporating multiple wells (and thus materials) into a single well assembly, allowing for parallel material analysis, further enabling high throughput material characterization using the described assay device.

Well 22 is designed to maximize internal well temperature while minimizing the temperature of the flange 32 where elastomeric seals must be reliable. It is desirable to use elastomeric seals at all component interfaces because they are relatively simple to implement and fairly inexpensive. However, elastomeric seals are less reliable in higher temperature ranges. One embodiment of elastomeric seal 46 as seen in FIG. 1A is preferably rated for temperatures of up to approximately 200° C. Other elastomeric seals may be available having different temperature ratings. It is desirable to keep the seal interface sufficiently below this temperature to provide reliable sealing. The well 22, as described herein, permits sample material 14 temperatures significantly above rated elastomeric seal temperatures.

As discussed above, to maximize heat transfer between the heater 120 and well 22, the area A2 of well 22 (as seen in FIG. 7B) should be maximized without compromising the internal volume of well 22. The thickness W of side wall 23 in the lower portion 37 of the well 22 (see FIG. 2B) should be maximized by minimizing inner well diameter DD without compromising the ability to synthesize material 14 in well 22. This is done to increase wall temperature along the height L of the lower portion 37 of the well 22, providing a larger cross-sectional area for heat transfer, resulting in a lower thermal resistance (due to the thicker wall) and higher heat capacity (due to the increased mass). As shown in FIG. 1A, wear plate 26 may protrude into well 22 when assembled, and its protrusion depth may match the step in wall thickness of well 22, as seen in FIG. 2A. This ensures that all material 14 is enclosed in the well region which has a thicker side wall 23. The upper portion of the well 22 has a significantly thinner wall thickness w to minimize heat transfer. The corresponding smaller cross-sectional area results in a higher thermal resistance and lower thermal mass, effectively minimizing heat into the well flange 32 and minimizing the temperature of elastomeric seal 46. The thickness of the bottom portion 25 of well 22 may also be minimized (while still safely allowing for desired pressures in well 22) to minimize thermal resistance between heater 120 and material 14.

In order to minimize temperature at the well flange 32, heat transfer out of the well flange 32 must be maximized. In particular, heat must be directed out of the well assembly 12 entirely; and in this case, into the temperature controlled block 110 of FIG. 7A. To accomplish this, several measures may be implemented. The flange 32 of well 22 has a relatively large outer diameter. This provides a large surface area and thus higher thermal transfer rate out of the well flange 32. The adapter 30 seen in FIG. 1A preferably consists of a material with high thermal conductivity to promote heat transfer out of well 22 and through flange adapter 30. For example, a common aluminum alloy may be used for adapter 30, as aluminum is a material with high thermal conductivity. To improve appearance and prevent corrosion, the adapter 30 may be surface coated with a noncorrosive finish; in this case anodize is used. However, to prevent additional thermal resistance due to surface coatings, adapter 30 may be left without surface coating on surface 42 (FIG. 1A) and surface 43 (FIG. 1B). This promotes heat transfer out of the well flange 32 and into the temperature controlled block 110 to which the well assembly 12 mates when installed in the temperature control assembly 17. For the same purpose, the surface coating in area 112 (FIG. 6B) of the temperature controlled block 110 may be omitted. Thus, thermal resistance between the well flange 32 and temperature controlled block 110 is minimized, and the interface of the well flange 32 and the adapter 30 as well as the interface of the adapter 30 and the temperature controlled block 110 promote efficient heat removal from the well flange 32 through adapter 30 to the temperature controlled block 110.

Referring to FIG. 7A, in order to minimize heat loss due to natural convection, a thermal insulator 134 within the temperature control assembly 17 encompasses an outer surface of the well 22. FIG. 7A illustrates a cross-sectional view in which insulator 134 can be seen surrounding well 22. The insulator 134 is preferably a material with low thermal conductivity which acts to trap heat between the well 22 and insulator 134, thereby minimizing heat loss through natural convection.

Referring to FIGS. 6A-7A, legs 135 support temperature controlled block 110 on base 137. Additional legs 138 support a spacer ring 139 that in turn supports the insulator 134. Hose adapters 145 may be mounted to the temperature controlled block 110 at channels 147 provided through the temperature controlled block 110. The hose adapters 145 may connect hoses used to route cooling or heating fluid between a chiller unit or heater/chiller unit (not shown) and the channels 147 of the temperature controlled block 110. A bayonet adapter 149 supports an optional thermocouple and threads into a thermocouple adapter 151 that mounts to the temperature controlled block 110.

The additive effects of the thermal transfer properties in key locations as described above allow for maximum efficiency of heat transfer through the well assembly 12, ultimately achieving the desired temperature of material 14 while allowing for elastomeric seals between some or all components. The well assembly 12 as described above allows for in-well material temperatures of approximately 550° C. with well flange 32 temperatures significantly below rated elastomeric seal temperatures. Other embodiments of a well assembly may allow for higher in-well material temperatures. The well assembly 12 also allows for in-well material synthesis (no material transfer required between synthesis and assay measurement) in synthesis devices such as ball mills.

Figure 8A:
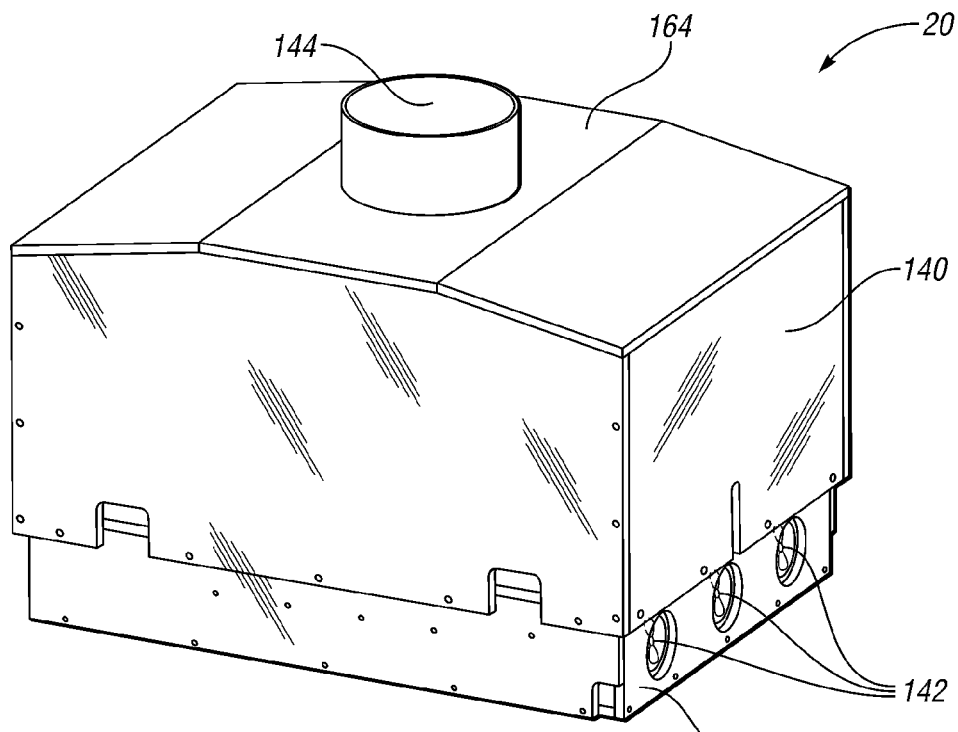
FIG. 8A is a schematic perspective illustration of a temperature controlled enclosure assembly including an enclosure.
Figure 8B:
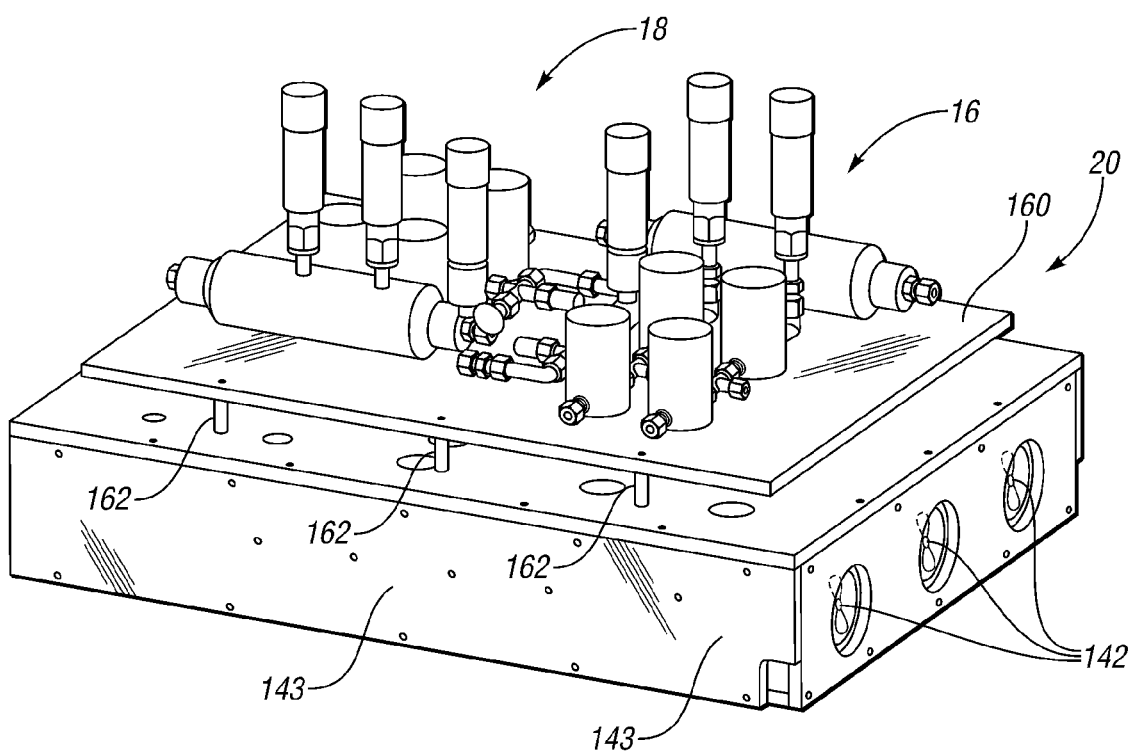
FIG. 8B is a schematic perspective illustration of the enclosure of FIG. 8A with enclosing walls and roof removed and showing a portion of a gas delivery control system with channels, valves and pressure transducers for controlling gas flow to the cap plate assembly and well assembly on the temperature control assembly of FIG. 6A.
Figure 13:
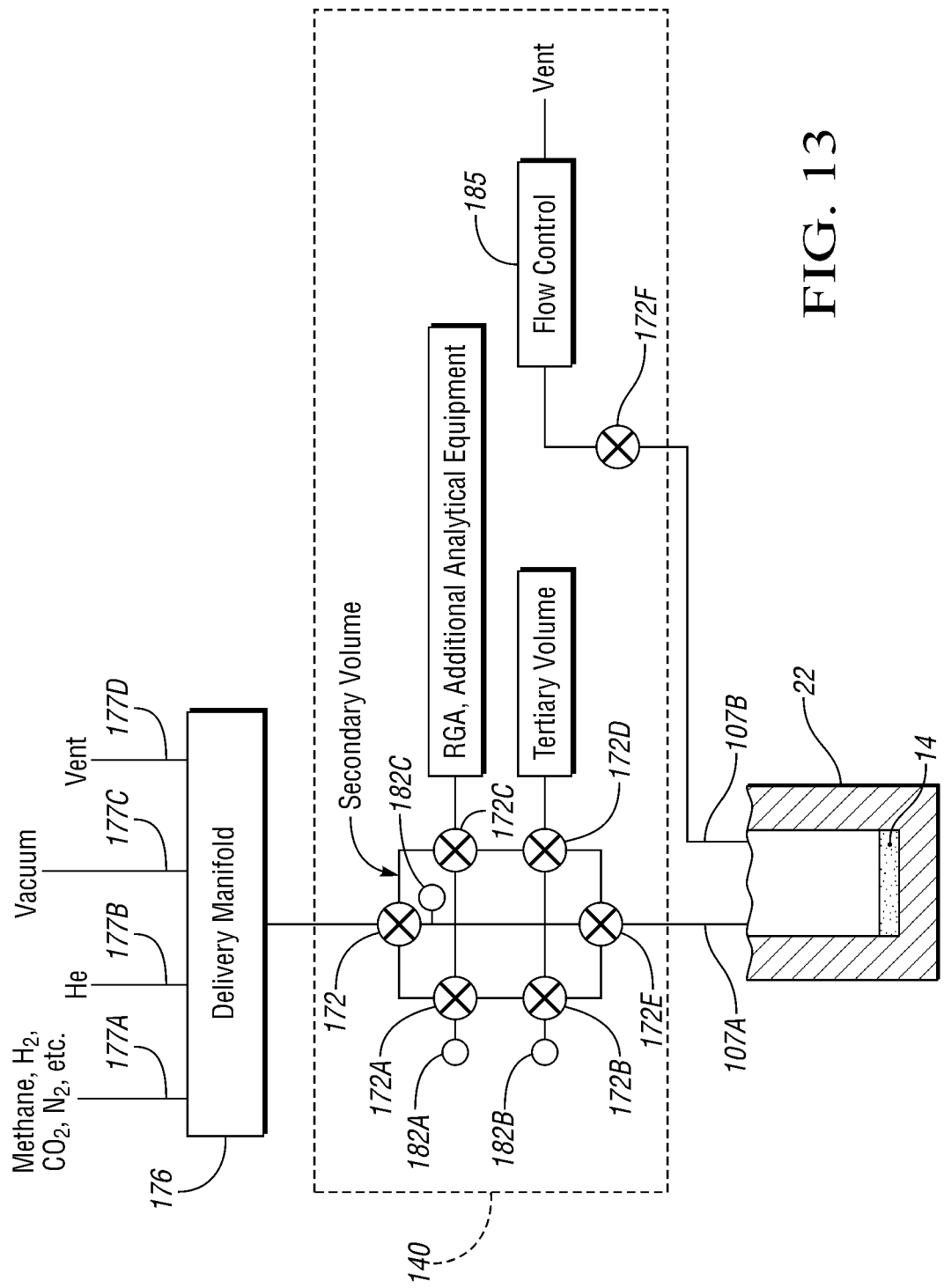
FIG. 13 shows a schematic illustration of a single channel of the gas delivery and control system.

In addition to the temperature control assembly 17, the measurement device 16 consists of the gas delivery and control system 18 which includes multiple measurement channels (allowing for high throughput material characterization, as multiple materials can be characterized in parallel), each of which is comprised of a number of valves, multiple known volumes, and several pressure transducers connected through multiple gas lines, as shown partially in FIG. 8B and schematically in FIG. 13. For accurate measurement, all of these components should be maintained at a known temperature with minimal fluctuations. Pressure traces over time and varying material temperatures (within well assembly 12) are used to characterize material properties. Any fluctuations in pressures due to temperature change of the gas contribute to pressure changes not associated with gas uptake or release from the subject material 14, resulting in larger measurement error. One way to overcome this obstacle is to enclose the gas delivery and control system 18 in a temperature controlled enclosure 140 (shown in FIG. 8A) of the temperature controlled enclosure assembly 20, in order to ensure a uniform, known temperature for all components and gas volumes with little to no temperature fluctuations.

Temperature Controlled Enclosure Assembly

FIG. 8A illustrates the enclosure 140 within which all temperature sensitive components are located. The enclosure 140 may be constructed in an appropriate size to include components for a multitude of channels, further contributing to the parallel testing, high throughput capability of the apparatus 10. Fans 142 mounted to a base 143 of the enclosure assembly 20 draw air into the enclosure 140, after which the air will be heated. Vent 144 allows for an exhaust circuit to continually draw air out of enclosure 140 such that any hazardous gas leaks are safely exhausted from the enclosure 140.

FIG. 8B depicts a view of the gas delivery and control system 18 mounted to the base 143 with the enclosure 140 removed.

Figure 9A:
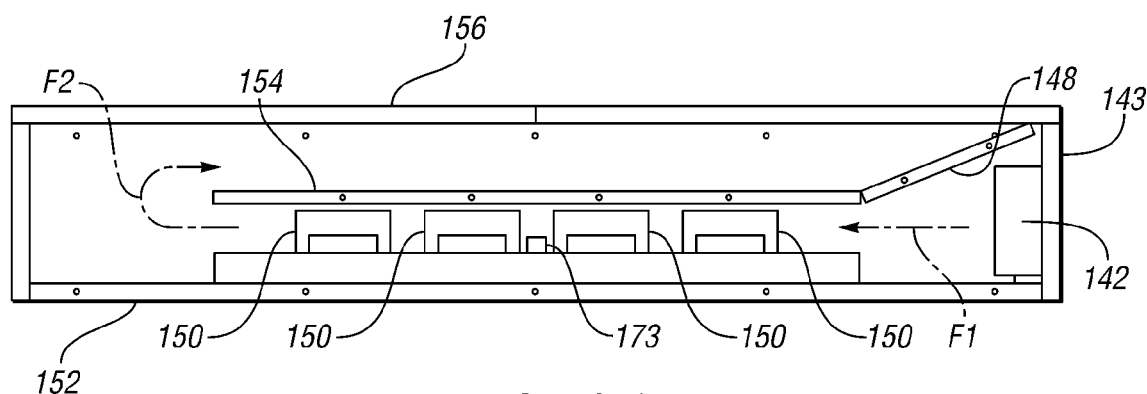
FIG. 9A is a schematic cross-sectional illustration of heaters and an air flow path in a base of the enclosure assembly of FIG. 8A with a wall removed.
Figure 9B:
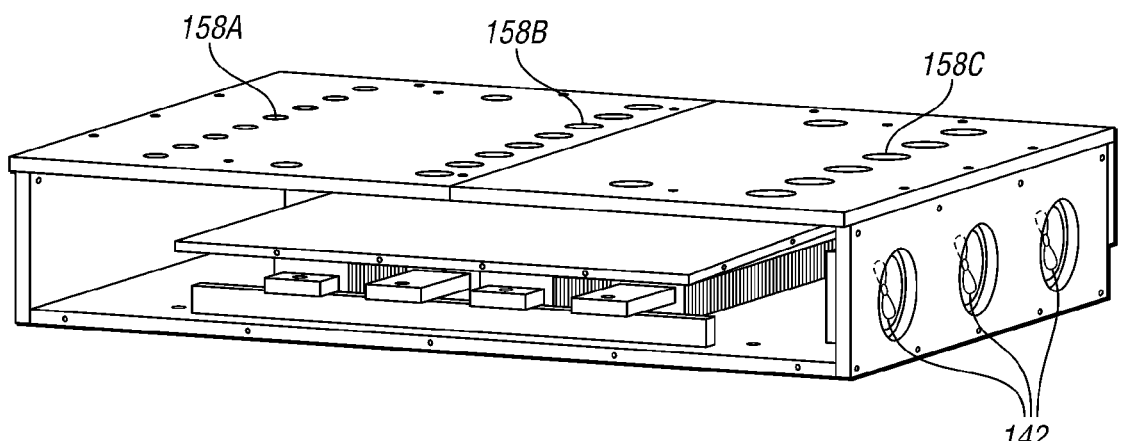
FIG. 9B is a schematic perspective illustration of the enclosure base of FIG. 9A with varying size air outlet apertures.

FIG. 9A illustrates the base 143 to show how air is heated within the enclosure 140. Air is drawn into the enclosure 140 through the fans 142, as indicated by air flow F1, and directed through a duct 148 containing a number of heated components 150 with surfaces that are controlled to a specific temperature. The heated air is then directed upwards through an abrupt change in direction, as indicated by air flow F2, ensuring a mixed air at uniform temperature. The air flow direction is determined by the lower plate 152, middle plate 154 (which partially forms duct 148) and insulating plate 156, each of which partially define the base 143. The air then travels through spaced sets of holes 158A, 158B and 158C in insulating plate 156, as seen in FIG. 9B. Preferably, insulating plate 156 is made of a material of low thermal conductivity to ensure that convective heat transfer, rather than conductive heat transfer, is the primary source of heat energy into the temperature controlled enclosure 140. Material options for insulating plate 156 include ceramics, poly(4,4'-oxydiphenylene-pyromellitimide), PEEK (polyaryletheretherketone), various polymers, aerogel, glass and the like. A suitable example of poly(4,4'-oxydiphenylene-pyromellitimide) is the polyimide film KAPTON® developed by DuPont and commercially available from DuPont Electronic Technologies in Circleville, Ohio. The holes 158A, 158B and 158C in insulating plate 156 increase in size from holes 158A to holes 158C, further down the air stream, to ensure a uniform flow of heated air through all holes, as the pressure will be greater at the smaller holes 158A than at the larger holes 158C. Components of the gas delivery and control system 18 within the temperature controlled enclosure 140 are installed on a base 160, as shown in FIG. 8B. The base 160 is further insulated from thermal conduction with a standoff 162 (i.e., spacers or legs) of low thermal conductivity, thus ensuring that the gas delivery and control system 18 components placed on base 160 are heated only through thermal convection. Material options for standoffs 160 include ceramics, poly(4,4'-oxydiphenylene-pyromellitimide), PEEK (polyaryletheretherketone), various polymers, aerogel, and the like. In one embodiment, it may be desirable to control the temperature of a surface near heaters 150 and characterize the enclosure internal air temperature based on the controlled temperature near the surface of heaters 150. In this embodiment, thermocouple 173 measures the temperature at a location near heaters 150 (as seen in FIG. 9A). This temperature measurement may provide feedback for a heating circuit (not shown) connected with heaters 150. By controlling the heaters 150 via the feedback temperature to the heating circuit, the temperature at the location of the thermocouple 173 is held substantially constant. Controlling the temperature at the location of the thermocouple 173 and controlling the air flow rate F1 over heaters 150 yields a certain air temperature within the temperature controlled enclosure. This method ensures consistent, reliable enclosure air temperatures because the feedback temperature is located near heaters 150 and the resulting air temperature is consistent so long as the heater temperature and air flow remain consistent. This embodiment allows for an air temperature within enclosure 140 with minimal fluctuations.

Figure 10A:
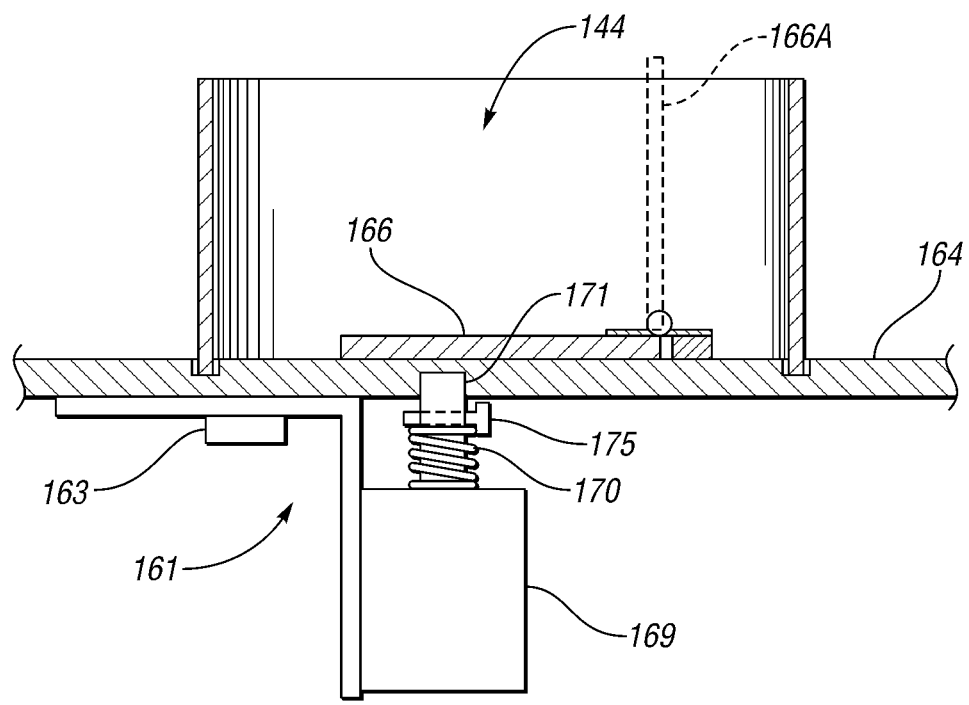
FIG. 10A is a schematic cross-sectional illustration of an actuatable vent cover located in exhaust stream on the roof of the enclosure, taken at the lines 10A in FIG. 10B.
Figure 10B:
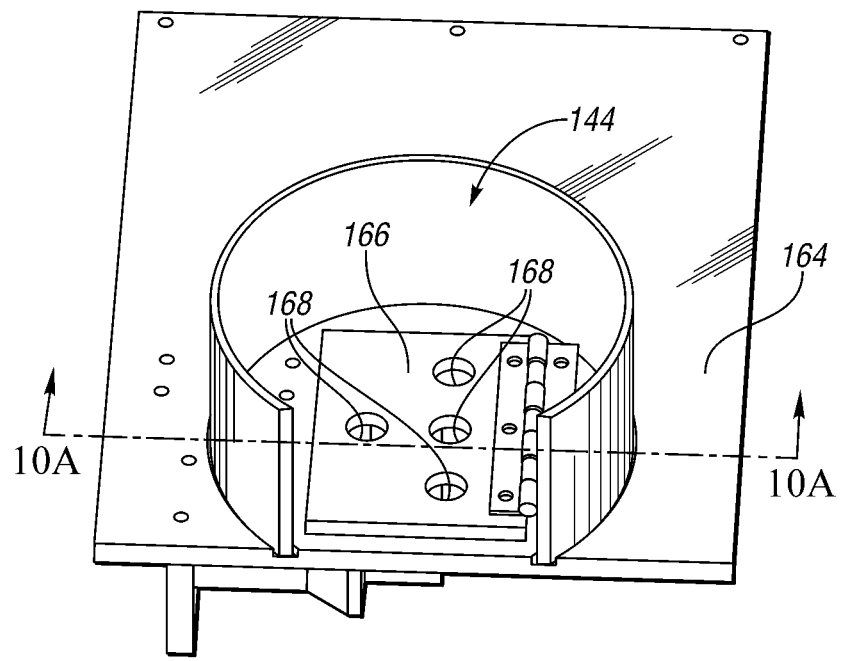
FIG. 10B is a schematic perspective illustration of the vent cover complete with holes for continuous air flow.

During operation, a multitude of hazardous gases may be present in the gas delivery and control system 18 and/or in the well assembly 12. Referring to FIG. 10A, due to the possibility of leaks in system connections and components, a hazardous gas detection system 161 may be implemented, which may include a sensor 163 mounted to the roof of the temperature controlled enclosure 140, as well as a door 166 pivotably hinged to the roof 164 at the vent 144. The sensor 163 is configured to sense a condition associated with an amount of one or more hazardous gasses. Those skilled in the art will be familiar with and will readily understand the function of such sensors. When a predetermined limit of hazardous gas in the air is detected by sensor 163, a relay is opened. This causes the emergency stop electrical circuit to be activated which immediately closes all valves in the system and opens door 166 of vent 144, shown in phantom in the open position 166A in FIG. 10A. This allows for rapid removal of air from inside the enclosure 140. The hazardous gas detection system 161 includes a linear solenoid 169 used in conjunction with a spring 170, as shown in FIG. 10. The spring is fastened to a rod 171 of the solenoid 169 with a fastener 175. When electrically powered, the downward magnetic force of the solenoid 169 is greater than the spring force of the compressed spring 170, and the solenoid rod 171 is retracted, thus allowing door 166 to close. Upon activation of the emergency stop circuit by the sensor 163, the solenoid 169 is powered off and the spring 170 overcomes the weight of the solenoid rod 171, which forces door 166 to the open position 166A. As shown in FIG. 10B, the trap door 166 has several holes 168, such that even when the door 166 is closed, air is vented from the enclosure 140 through the door 166, and may be actively pulled from the enclosure 140 by an exhaust system. Preferably, the holes 168 are covered with a porous material, such as a screen or filter, with the selected porosity serving to adjust the air flow rate to a desired rate.

Gas Delivery and Control System

FIG. 13 illustrates a preferred layout of gas lines and associated components of a single channel within the gas delivery and control system 18. Preferred embodiments may comprise multiple channels allowing for parallel measurement of multiple materials. As shown in FIG. 13, the majority of components of the gas delivery and control system 18 are contained within the dashed line representing the enclosure 140, indicating that they reside within the temperature controlled enclosure 140.

A delivery manifold 176 has four incoming channels 177A-177D which connect through valves to a common outlet. One channel 177A provides for incoming gas supply such as hydrogen, $CO_2$, methane, Nitrogen, etc. Another channel 177B provides for incoming helium supply, which is frequently used for leak checking the device. Helium is also often used for determining the volume within gas lines including the free space within well 22 surrounding sample material 14. This volume is required to determine adsorption characteristics for material 14. A third channel 177C provides communication with a vacuum pump, used to evacuate desired volumes within the device. A fourth channel 177D may connect to a vent, through which all gas is released from the system gas lines. Each channel may include at least one valve to control gaseous communication. Suitable valves may include ball valves, gate valves, solenoid valves, rotary valves, diaphragm valves, needle valves and the like.

Each channel may contain a number of pressure sensors (shown in FIG. 13 as 182A, 182B and 182C) whose pressure ranges and accuracies can be selected based on the intended uses for the assay device. Valves 172A and 172B control flow to pressure sensors 182A and 182B, respectively. Suitable pressure sensors for this application are known to those skilled in the art.

A preferred embodiment may include a valve 172C providing connection to a number of components including, but not limited to, a mass spectrometer (or similar gas composition measurement device), an additional pressure sensor or an additional volume to contain gas during a measurement.

The gas delivery and control system 18 may include a valve 172D, which provides similar function as valve 172C and may connect to an additional volume which may be required for assay processes requiring more moles of gas.

During an assaying process (or a synthesis process, if synthesis under gas flow is used), when gas enters the device 16, it enters only the secondary volume (the volume between valves 172 and 172E with all valves closed) or both the secondary and tertiary volumes (in which case valve 172D would be open when gas is dosed into the system). During gas dosing, additional valves may also be open. Valve 172A may be open if the pressure range of sensor 182A encompasses the desired dose pressure. In the same manner, valve 172B may also be open for sensor 182B to measure system pressure. After the desired dose pressure is met, valve 172 is closed and pressure is allowed to stabilize. Valve 172E is then opened and gas is allowed to expand into well 22 and the pressure sensors are in gaseous communication with the material 14 in well 22. The pressures are then observed for a given period of time and the change in pressure is used to quantify the gas uptake or release from material 14 at various temperatures. It may be desirable to open valve 172C to provide gaseous communication to additional analytical equipment, such as a residual gas analyzer that could measure gas compositions for any mixed gases with the system 18. The outgoing line of 107B (shown also in FIGS. 5B and 6A) routes to valve 172F. When the outgoing valve 24B in FIG. 2A is opened (as shown in FIG. 3A) and valve 172F is opened, gas is allowed to flow through the well assembly 12 and out of the system vent. An adjustable flow control 185 after valve 172F allows for fine tuning of gas flow rates through the outgoing line 107B. It is desirable to have capabilities of gas flow over a sample of material 14, as some storage materials require a low gas flow rate across the material during synthesis. Having the capability of gas flow allows for some material synthesis to be conducted in the same device performing the assay, improving efficiency of material characterization, thus enhancing the high throughput nature of the assay device.

The device 16 is also capable of gas turnover in pulses by opening and closing of valve 172F at a predetermined frequency to produce a desired gas turnover rate. For example, heat treatment of a number of materials is one process in which the synthesis requires a high temperature (often above 300° C.) as well as a gas flow across the material 14.

Dual valves 24A, 24B in lid assembly 15 of FIG. 1A may be opened and closed in an automated fashion, rather than through the use of the actuator pins 96A, 96B and cam devices 105A and 105B of cap plate assembly 84 of FIG. 4A. Automating the motion of the actuator pins may improve efficiency of the assay device, allowing for fully automated software procedures to be conducted.

In alternate embodiments, a process to turn over the gas within the well assembly 12 through use of only the inlet valve 24A may be implemented. Rather than flowing gas through the well assembly 12 (which requires both an inlet and outlet), gas is continually dosed into the well assembly 12 at a given pressure, and then vented and vacuumed solely through the inlet valve 24A. The process may be referred to as pulsing the gas through the well assembly 12. Pulsing allows for continual turnover of the gas surrounding the material 14 in the well 22, and acts to remove any gases emitted during material synthesis performed in the well assembly 12. The time period between pressure dosing and venting is a parameter variable that can be changed for various processes requiring pulsing. The pulsing process may eliminate the need for an outlet valve from the well assembly 12, possibly reducing costs and complexity of the assay device.

Potential Applications of the Measurement Device

The device 16 may be used for a variety of assaying applications with little or no modification. Exemplary applications include the evaluation of materials for gas/vapor separation, for hydrogen storage, for capture of carbon dioxide (i.e., a specific example of gas separation), for gas/vapor purification, for catalysis when one of the reagents is in the gas phase. Furthermore, the device 16 may be used to test the thermal stability of materials where decomposition produces or consumes a gas (e.g. oxygen evolution in battery electrodes, outgassing of polymers, any combustible material), for in situ synthesis and assaying of activated carbons, intermetallics, etc. The device 16 may be used to measure the active surface area of catalysts, the surface area, pore size, and pore size distribution of porous materials, the enthalpy and entropy of sorption of a gas sorbing onto a material, and the kinetics of sorption (including activation energy).

The device 16 can be modified to incorporate a device that enables measurement of gas composition, such as a mass spectrometer, infrared spectrometer and the like. Some applications, such as gas separations, require measurement of gas composition and its change during gas uptake or release from the material being characterized.

While the best modes for carrying out the invention have been described in detail, those familiar with the art to which this invention relates will recognize various alternative designs and embodiments for practicing the invention within the scope of the appended claims.

The invention claimed is:

1. An apparatus for material synthesis and assaying comprising:
a well assembly having a well that is configured to contain material and gas for use in measuring at least one property of the material; wherein the well assembly is configured such that the material is synthesized within the well; wherein the well has a bottom portion, a side wall extending from the bottom portion, and a generally annular flange extending circumferentially around and outward from the side wall;
a generally annular adapter abutting the flange;
a measurement device operatively connected to the well assembly;
wherein the measurement device includes a temperature control assembly that has a block; wherein the block has a surface that abuts a surface of the adapter; and wherein the adapter is characterized by a thermal conductivity greater than a thermal conductivity of the flange to promote heat transfer between the flange and the block.

2. The apparatus of claim 1, wherein the temperature control assembly has a heater positioned in contact with the bottom portion to heat the well.

3. The apparatus of claim 2, wherein the heater is in contact with the bottom portion and the side wall.

4. The apparatus of claim 2,
wherein the heater is positioned in contact with the bottom portion and not in contact with the side wall; wherein the bottom portion is characterized by a surface area in contact with the heater; wherein the side wall is characterized by a cross-sectional area generally perpendicular to the depth of the well; and
wherein the cross-sectional area of the side wall is a predetermined maximum size that provides a predetermined minimum internal volume of the well to promote heat transfer from the heater to the well and reduce a temperature gradient in the bottom portion.

5. The apparatus of claim 2, wherein the temperature control assembly further includes a spring biasing the heater against the well.

6. The apparatus of claim 2, wherein the well assembly further includes:
a wear plate having a flange portion and a protruding portion; and
an elastomeric seal supported at the flange and configured to seal the flange to the flange portion of the wear plate when the wear plate is placed on the flange with the protruding portion extending into the well.

7. The apparatus of claim 6, wherein the adapter has a stepped opening configured such that the side wall of the well extends through the stepped opening when the flange abuts the adapter at the stepped opening.

8. The apparatus of claim 6, wherein the abutting surfaces of the adapter and the block are uncoated to further promote heat transfer between the flange and the component.

9. The apparatus of claim 2, wherein the heater is in contact with the bottom portion; and wherein the well has a step at an inner diameter such that a thickness of the side wall at the flange is less than a thickness of the side wall adjacent to the bottom portion, thereby minimizing heat transfer from the well to the flange.

10. The apparatus of claim 2, wherein the well has a step at an inner diameter; wherein the well assembly includes a wear plate configured to fit with the well at the stepped diameter and to protrude into the well at the step, thereby maintaining the material in a portion of the well between the step and the bottom portion.

11. The apparatus of claim 2, wherein the temperature control assembly further includes an insulator configured to at least partially surround an outer surface of the side wall of the well to minimize heat transfer from the well through the side wall.

12. The apparatus of claim 2, wherein the apparatus further includes first and second valves openable and closable to control the flow of gas from the measurement device into and out of the well; and wherein the apparatus is configured to provide synthesis of the material within the well while gas flows through the well when the first and the second valves are open.

13. An apparatus for material synthesis and assaying comprising:
a well assembly having a well that is configured to contain material and gas for use in measuring at least one property of the material;
a measurement device operatively connected to the well assembly;
wherein the well has a flange extending at least partially circumferentially therearound, and wherein the well assembly further includes:
a wear plate; and
an elastomeric seal supported at the flange and configured to seal the flange to the wear plate;
a generally annular adapter abutting the flange;
a temperature control assembly including a block that has a surface in contact with a surface of the adapter; and
wherein the adapter is characterized by a thermal conductivity greater than a thermal conductivity of the flange to promote heat transfer between the flange and the block.

14. The apparatus of claim 13, wherein the apparatus further includes first and second valves openable and closable to control a flow of gas from into and out of the well; and wherein the apparatus is configured to provide synthesis of the material within the well while gas flows through the well when the first and the second valves are open.

15. An apparatus for material synthesis and assaying comprising:
- a well assembly having a well that is configured to contain material; wherein the well assembly is configured such that the material is synthesized within the well;
- a measurement device operatively connected to the well assembly and configured to provide gas flow to the well for use in measuring at least one property of the material in the well; wherein the measurement device includes a temperature control assembly having a heater positioned to heat the well; wherein the apparatus is operable at temperatures within the well greater than about 550 degrees Celsius and pressure within the well greater than about 150 Bar;
- wherein the well has a bottom portion, a side wall extending from the bottom portion, and a flange extending at least partially around the well;
- a generally annular adapter abutting the flange; wherein the temperature control assembly has a block that has a surface that abuts a surface of the adapter; wherein the adapter is characterized by a thermal conductivity greater than a thermal conductivity of the flange to promote heat transfer between the flange and the block;
- wherein the heater is in contact with the bottom portion;
- wherein the well has a step at an inner diameter such that a thickness of the side wall at the flange is less than a thickness of the side wall adjacent to the bottom portion, thereby minimizing heat transfer from the well to the flange; and
- wherein the well assembly includes a wear plate configured to fit with the well at the stepped diameter and to protrude into the well at the step, thereby maintaining the material in a portion of the well between the step and the bottom portion.

16. The apparatus of claim 15, wherein the apparatus includes first and second valves openable and closable to control the flow of gas from the measurement device into and out of the well; and wherein the apparatus is configured to provide synthesis of the material within the well while gas flows through the well when the first and the second valves are open.

* * * * *